United States Patent [19]
Oshima et al.

[11] Patent Number: 5,840,555
[45] Date of Patent: Nov. 24, 1998

[54] TRANSCRIPTIONAL REGULATORY REGIONS DERIVED FROM THE K18 GENE

[75] Inventors: Robert G. Oshima, Encinitas; Nickolay S. Neznanov; Grace Cecena, both of San Diego, all of Calif.

[73] Assignee: La Jolla Cancer Research Foundation, La Jolla, Calif.

[21] Appl. No.: 486,148

[22] Filed: Jun. 7, 1995

Related U.S. Application Data

[63] Continuation of Ser. No. 146,486, Oct. 29, 1993, abandoned.
[51] Int. Cl.$^6$ .............................. C12N 5/00; C12N 15/00; C07H 21/04
[52] U.S. Cl. .................................... 435/172.3; 435/320.1; 435/325; 536/24.1; 935/6; 935/22; 935/36; 935/70
[58] Field of Search ................................. 536/24.1, 23.5; 435/240.2, 172.3, 320.1; 800/2, DIG. 1; 935/6, 22, 36, 70

[56] References Cited

PUBLICATIONS

Howard and Sakamoto, "ALU Interspersed Repeats: Selfish DNA or a functional gene family?" *The New Biologist.* 2(9):759–770 (1990).
Braun et al., "Infertility in male transgenic mice: Disruption of sperm development by HSV–tk expression in postmeiotic germ cells". *Biol. of Reproduction* 43:684–693 (1990).
Labarca and Paigen, A simple, rapid, and sensitive DNA assay procedure. *Analytical Biochem.* 102:344–352 (1980).
Chirgwin, et al., "Isolation of biologically active ribonucleic acid from sources enriched in ribonuclease". *Biochem.* 18(24):5294–5299.
Oshima et al., "Comparison of mouse and human keratin 18: a component of intermediate filaments expressed prior to implantation". *Differentiation* 33:61–68 (1986).
Bradford, "A rapid and sensitive method for the quantitation of microgram quantities of protein utilizing the principle of protein–dye binding". *Analytical Biochem.* 72:248–254 (1976).
Perez–Stable and Shen, "Competitive and cooperative functioning of the anterior and posterior elements of an Alu family repeat". *Molecular and Cellular Biology* 6(6):2041–2052 (1986).
Kulesh and Oshima, "Cloning of the human keratin 18 gene and its expression in nonepithelial mouse cells". *Molecular and Cellular Biology* 8(4):1540–1550 (1988).
Al–Shawi, "Expression of a foreign gene in a line of transgenic mice is modulated by a chromosomal position effect". *Molecular and Cellular Biology* 10(3):1192–1198 (1990).
Reynolds and Johnson, "Differential expression of oocyte–type class III genes with fraction TFIIIC from immature or mature oocytes". *Molecular and Cellular Biology* 12(3):946–953 (1992).
Sanger et al., "DNA sequencing with chain–terminating inhibitors". *Proc. Natl. Acad. Sci. USA* 74(12):5463–5467 (1977).
Celada and Maki, "The expression of I–A correlates with the uptake of interferon–γ by macrophages*". *Eur. J. Immunol* 19:205–208 (1989).
Jamieson and Subak–Sharpe, "Biochemical studies on the herpes simplex virus–specified deoxyprimidine kinase activity". *J. gen. Virol* 24:481–492 (1974).
Dudov and Perry, "The gene family encoding the mouse ribosomal protein L32 contains a uniquely expressed intron–containing gene and an unmutated processed gene". *Cell* 37:457–468 (1984).
Kulesh and Oshima, "Complete structure of the gene for human keratin 18". *Genomics* 4:339–347 (1989).
Kariya et al., "Revision of consensus sequence of human Alu repeats– a review". *Gene* 53:1–10 (1987).
Abe and Oshima, "A single human keratin 18 gene is expressed in diverse epithelial cells of transgenic mice". *The Journal of Cell Biology* 11:1197–1206 (Sep. 1990).
Thomas and Capecchi, "Site–directed mutagenesis by gene targeting in mouse embryo–derived stem cells". *Cell* 51:503–512 (Nov. 6, 1987).
Neznanov and Oshima, "cis Regulation of the keratin 18 gene in transgenic mice". *Mol. and Cell. Biol.* 13(3):1815–1823 (Mar. 1993).
Turpen et al., "Rapid isolation of RNA by a guanidinium thiocyanate/cesium chloride gradient method". 4(1):11–15 (1986).
JA Loudon et al (1993) Clinical Experimental Pharmacology Physiology 20:283–288.

*Primary Examiner*—Bruce R. Campbell
*Attorney, Agent, or Firm*—Campbell & Flores LLP

[57] ABSTRACT

The present invention provides DNA fragments derived from the 5' and 3' flanking regions of K18 gene which contain transcriptional regulatory regions capable of conferring integration site independent and copy number dependent expression on a transgene when co-integrated 5' and 3' of the transgene. The present invention also provides vectors containing these DNA fragments, and transgenic animals containing the vectors.

12 Claims, 15 Drawing Sheets

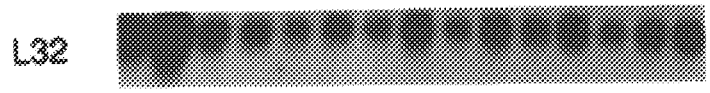
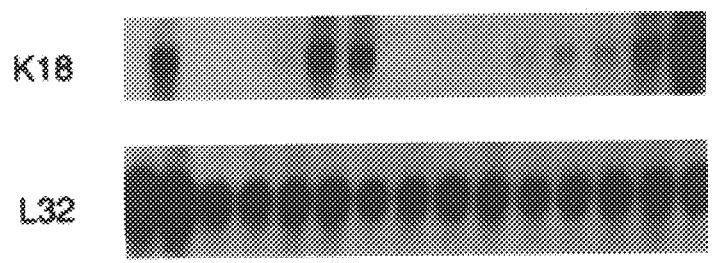
FIG. 4A
FIG. 4B
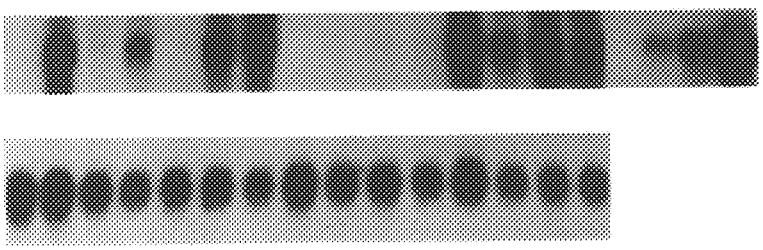
FIG. 4C

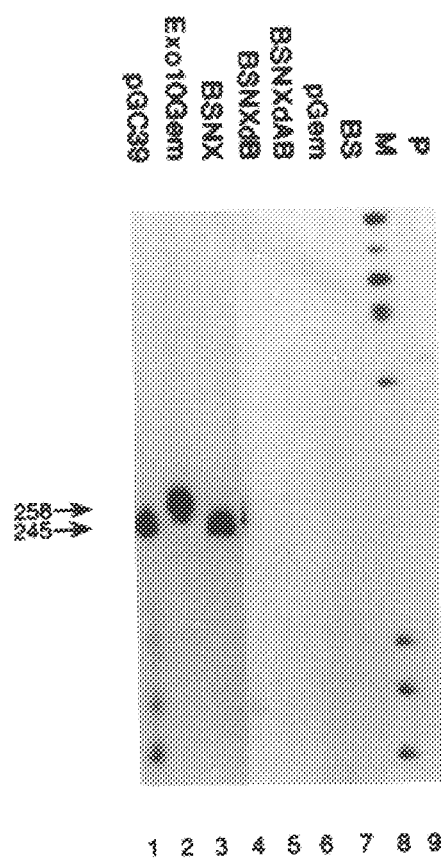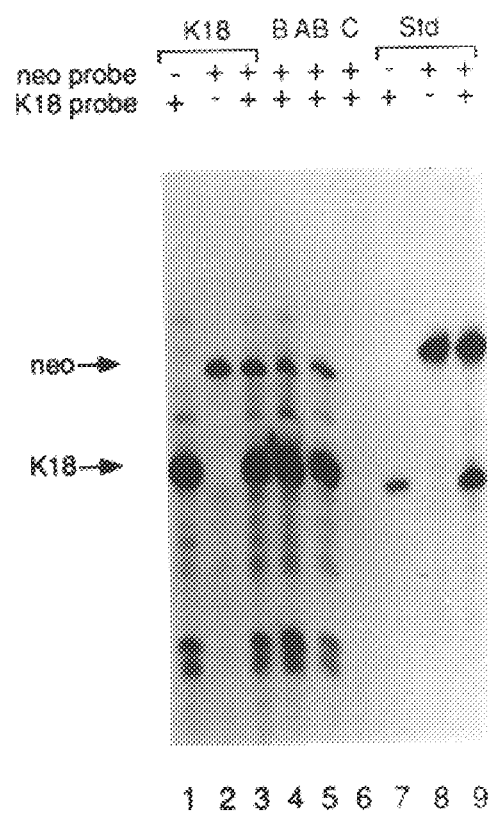
FIG. 5B
FIG. 5C

K18 gene

```
CATTCCCTGT CCAAATCACA GTGTTCCACT GAGGCAAGGC CCTTGGGAGT GAGGTCGGGA     60
GAGGGAGGG  TGGTGGAGGG GGCTCAGAGA CTGGGTTTGT TTTGGGGAGT CTGCACCTAT    120
TTGCTGAGTG AATGTATGTG TGTGTGCATT TGAGAGCACA CCTCTGTATG ATTCGGGTGT    180
GAGTGTGTGT GAGGAAACGT GGGCAGGCGA GGAGTGTTTG GGAGCCAGGT GCAGCTGGGG    240
TGTGAGTGTG TAAGCAAGCA GCTATGAGGC TGGGCATTGC TTCTCCTCCT CTTCTCCAGC    300
TCCCAGCCTT TCTTCCCCGG GACTCCTGGG GCTCCAGGAT GCCCCAAGA  TCCCCTCCAC    360
AAGTGGATAA TTTGGGCTGC AGGTTAAGGA CAGCTAGAGG GACTCACAGG CCATTCCACC    420
CGCACACCAC CAGACCCCCA AATTTCTTTT TTCTTTTTTT TTTGAGACAG AGTCTCACTC    480
TGTCGCCAGG CTGCAGTGGC GCGATCTCGG CTCACTGCAA CCTCCGCCTC CCAGGTTCAA    540
GCGATTCCCC TTCCTCAGCC TCCCAAGTAG CTGAGACTAC AGGCGTGCAC CATCACGTCC    600
GGCTAATTTT TTGTATTTTA GTAGAGAGGG GTTTCACCAT GTTGGCTAGG ATGGTCTCGA    660
                                                        B-BOX
TCTCCTGACC TCGTGATCCG CCCACCTAGG CCTCCCAAAG TGCTGAGATT ACAGGCGTGA    720
A-BOX
GCCACTGCGC CCGGTCAAGA CTCCCAAATT TCAAACTCGC CAGCACCTCC TCCACCTGGG    780
GGAGAAGAGC ATAATAACGT CATTTCCTGC CCTGAAAGCA GCCTC                    825
```

FIG. 9

TRANSCRIPTIONAL REGULATORY REGIONS DERIVED FROM THE K18 GENE

This application is a continuation of application Serial No. 08/146,486, filed Oct. 29, 1993 abandoned.

This invention was made with the support of government grant CA 42302 from the National Institute of Health. Therefore, the United States government may have certain rights to this invention.

BACKGROUND OF THE INVENTION

Eukaryotic genes are regulated by the interaction of transcription factors with their DNA binding sites and with the interactions of the transcription factors with each other. Some transcriptional regulator elements are able to function relatively independently of their orientation and position in the chromosome. Some regulatory elements are located at a great distance from the proximal promoter of the genes they control. Some elements participate in the regulation of more than one gene. Special chromosomal structures have been identified which are thought to represent regulatory domains, such as chromosomal loops or the chromatin structures found in *Drosophila melanogaster*. More precise regulation of genes, however, is thought to involve cis-acting regulatory elements.

The effect of cis-acting regulatory elements can be clearly seen when foreign genes are introduced into eukaryotic organisms. The integration of foreign genes into transgenic animals such as transgenic mice will often result in changes in the level of expression of the gene as well as the tissue specificity of expression of the gene. These changes may be due to endogenous cis-acting regulatory elements flanking the sites of integration.

The human keratin (K18) gene codes for a type I keratin intermediate filament protein that is first expressed just prior to the blastocyst stage and later in a variety of embryonic and adult simple (single-layered) epithelia, including intestine, lung, liver, kidney, and the ependymal cell layer of the brain. The tissue specific expression of the K18 gene appears to be due, at least in part, to its chromatin state, which may limit accessibility of necessary transcription factors.

It has been found that a 10 kb fragment of the K18 gene contains sufficient information to ensure both adult tissue specificity and appropriate developmental expression. This 10-kb K18 gene has been readily expressed in a number of transgenic mouse lines. Analysis of the mouse lines carrying the human K18 gene shows appropriate, tissue-specific, and copy-number-dependent expression of this gene. The 10-kb K18 gene is expressed in a variety of internal epithelial organs in the mouse, including liver, lung, intestine, kidney, and the ependymal epithelium of brain, but not in spleen, heart or skeletal muscle. The K18 gene was expressed in every transgenic mouse line, independent of the different sites of integration. It has further been established that the level of K18 RNA is directly proportional to the number of transgenes and comparable, on a per gene basis, to the level of expression of the endogenous gene.

An understanding of the control of foreign gene expression in transgenic animals is important for improving desired transgene expression in such animals. The isolation of regulatory elements capable of controlling the expression of a variety of transgenes would be extremely useful for controlling and facilitating the expression of transgenes in animals or for controlling gene expression for gene therapy purposes. Furthermore, the most effective use of transgenes requires an understanding of how to insulate the gene from adjacent regulatory regions at the site of integration, and how inappropriate interaction between regulatory elements of each copy of the tandemly duplicated transgene normally found in transgenic mice can 35 be prevented. Therefore, there exists a need to isolate and characterize regulatory elements capable of controlling gene expression not only for the gene with which they are associated, but for other, unrelated, genes as well. The present invention fulfills this need, and provides related advantages as well.

SUMMARY OF THE INVENTION

The present invention provides DNA fragments which contain gene regulatory regions capable of controlling site-independent and copy number-dependent expression of transgenes when co-integrated with the transgene into a chromosome. Vectors containing these regulatory fragments, and transgenic animals generated using these vectors have also been provided.

BRIEF DESCRIPTION OF THE DRAWINGS

FIGS. 4A–4C show Northern blot analysis of RNAs of K18-NX, K18-XX and K18-NBX transgenic lines hybridized with a K18 probe and a L18 probe for liver (FIG. 4A), intestine (FIG. 4B), and kidney (FIG. 4C).

FIG. 5B shows an RNAase protection analysis of Alu transcription in vitro using the plasmids of FIG. 5A; and FIG. 5C shows an RNAase protection analysis of the RNA produced when an HR9 cell line was transfected with the K18 constructions of FIG. 1.

FIG. 6A shows an autoradiograph after hybridization with a K18 probe; and FIG. 6B shows an autoradiograph after hybridization with L32 ribosomal protein probe.

FIG. 7A shows an autoradiograph after hybridization with a K18 probe, and FIG. 7B shows an autoradiograph after hybridization with an L32 ribosomal probe.

FIG. 9 shows the DNA sequence for the 825 base pair K18 5' flanking fragment.

FIG. 14A shows the relative levels of TK RNA, FIG. 14B shows enzyme activity in the testes of transgenic males compared with the copy number of the NNTK mouse lines, and FIG. 14C shows TK brain RNA compared with the copy number of independent lines.

DETAILED DESCRIPTION OF THE PREFERRED EMBODIMENTS

Figure 1:
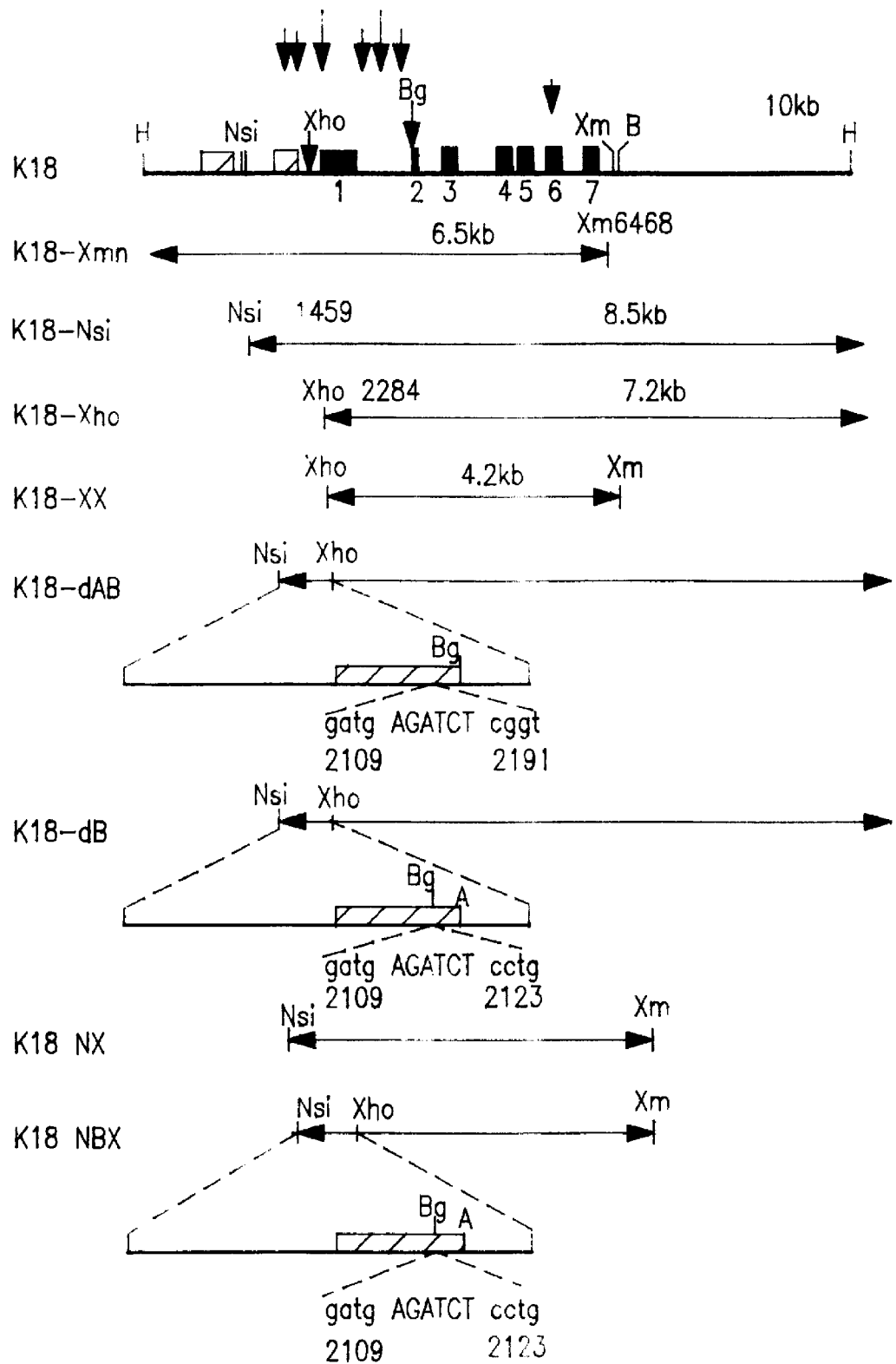
FIG. 1 shows the K18 gene constructions which were tested in transgenic mice.

The present invention provides DNA fragments which contain transcriptional regulatory regions capable of controlling site-independent and copy number-dependent expression of transgenes when co-integrated with the transgene into the chromosomes of an animal. Vectors containing these DNA fragments, and transgenic animals containing the integrated vectors including these fragments are also provided.

Definitions

As used herein, the term "transgene" refers to a fragment of DNA which codes for a specific protein or RNA product and which is capable of becoming integrated into at least one chromosome of an organism. The transgene DNA includes the promoter region from the same gene or another gene. The transgene DNA can be obtained from another species or the same species as the host organism, and is introduced into embryos or cells as cloned, purified DNA as opposed to chromosomes or fused cells. Integrated transgenes have been shown to exist as tandomly duplicated gene arrays within the host chromosome.

As used herein, the term "transcriptional control element" or "transcriptional regulatory element" refers to a specific DNA sequence which functions in assembling or modulating the complex of proteins involved in ensuring that the DNA of a gene is copied into an mRNA. The regulatory elements are commonly, but not exclusively, targets for the binding of proteins important for the assembly or modulation of the transcription complex.

As used herein, the term "cis-acting regulatory elements" refers to regulatory elements which flank the sites of integration of foreign genes and are considered to be responsible for differences in levels of expression or in tissue specificity, such as described in Al-Shawi et al., Mol. Cell. Biol. 10:1192–1198 (1990), which is herein incorporated by reference.

As used herein, the term "copy number-dependent expression" refers to the expression of transgenes within a tissue which is linearly proportional to the number of integrated copies of the gene. Copy number-dependent expression indicates each copy of the tandomly duplicated gene arrays of integrated transgenes can function independently of not only the site of integration of the array, but also independently of each neighboring copy of the same gene. Copy number-dependent expression can be deduced from the relationship between transcriptional efficiency and increasing copy number, as described in more detail below.

As used herein, the term "tissue-specific expression" refers to the expression of a transgene in a specific set of differentiated cell types. For example, the human keratin K18 gene in humans and the endoB gene in mice are expressed in a variety of simple epithelial tissues including liver, intestine, kidney, lung, and the ependymal layer of the brain, but not in mesodermally derived tissues such as skeletal muscle, heart or lymphoid tissues such as spleen.

As used herein, the term "integration site-independent expression", "site independent expression" or "position independent expression" refers to the expression of a transgene regardless of the location in a chromosome into which it becomes integrated. Position independent expression indicates that the integrated transgene has become insulated from adjacent endogenous regulatory regions at the site of integration. Generally, integration site-independent expression of a transgene can be assumed if every or almost every transgenic founder animal expresses the transgene.

As used herein, the term Alu type repetitive DNA sequences refers to a type of repetitive DNA sequence which is transcribed as a unit, and for which the function is not yet understood. See, for example, Kariya et al., Gene 53:1–10 (1987), which is herein incorporated by reference. These sequences include a bipartite internal promoter for RNA polymerase III, the A element or box and the B element or box. The A box and B box represent regulatory DNA sequence elements which mediate the formation of the RNA polymerase III complex which then initiates transcription of the Alu sequence into RNA. This is described in detail in Howard et al., New Biologist 2:759–770 (1990), which is herein incorporated by reference.

The present invention provides DNA fragments which contain transcriptional regulatory regions capable of controlling copy number-dependent expression and integration site-independent expression of transgenes. These DNA fragments are derived from the distal flanking fragments of the human keratin 18 gene (referred to as the K18 gene). They are an 825 base pair (bp) fragment of the 5' flanking sequence and a 3.5 kilobase (kb) fragment of the 3' flanking sequence.

The sequence of the entire coding region of the K18 gene has previously been determined. As described in Kulesh et al., Genomics 4:339–347 (1989), which is herein incorporated by reference, the coding portion of the K18 gene is 3791 bp in length and contains seven exons. The exon structure has been conserved compared to that of other keratin genes. The gene contains two repetitive Alu transcription units upstream from the transcription start site. One Alu sequence, the proximal Alu sequence, is located approximately 300 base pairs upstream of the transcription start site. The translation initiation codon (ATG) that begins the open reading frame of exon 1 for the entire K18 gene is at nucleotide 2533 using the continuous numbering convention.

The present invention establishes that the 5' flanking 825 bp fragment and the 3' 3.5 kb flanking region each independently influence site-independent expression. Site-independent expression of a transgene will proceed in transgenic mice if either the 825 bp fragment or the 3.5 kb fragment is flanking the transgene in the 5' or 3' position respectively, but not if both are missing.

The functions of the K18 regulatory regions provided by the present invention have been established by constructing vectors having various deletions in the K18 3' and 5' flanking regions as shown in FIG. 1.

Transgenic mouse strains containing each of these were then generated according to the procedures described below. K18-specific RNA expression was then determined in various mouse organs of each mouse strain.

Unexpectedly every transgenic animal from each of the active K18 gene fragments shown in FIG. 1 expressed the K18 gene. Of these, only the K18-XX fragment appeared to be sensitive to the site of integration. This fragment is missing both the 5' and 3' flanking fragments. In contrast, the most closely related fragment, the K18-NX fragment, expressed in every integration site found. Therefore, the region defined by the difference between these two fragments, the 825 bp region between the proximal NsiI site and the XhoI site just upstream of the transcriptional start site, is necessary for integration site-independent expression of the K18 gene. However, transgenic mice containing constructs without this 825 bp region, but containing the 3.5 kb 3' flanking fragment, such as K18-Xho containing mice (see FIG. 1) also exhibited integration site-independent expression. Therefore, the present invention establishes that both fragments independently confer integration site-independent expression on the transgene they are flanking.

Figure 5A:
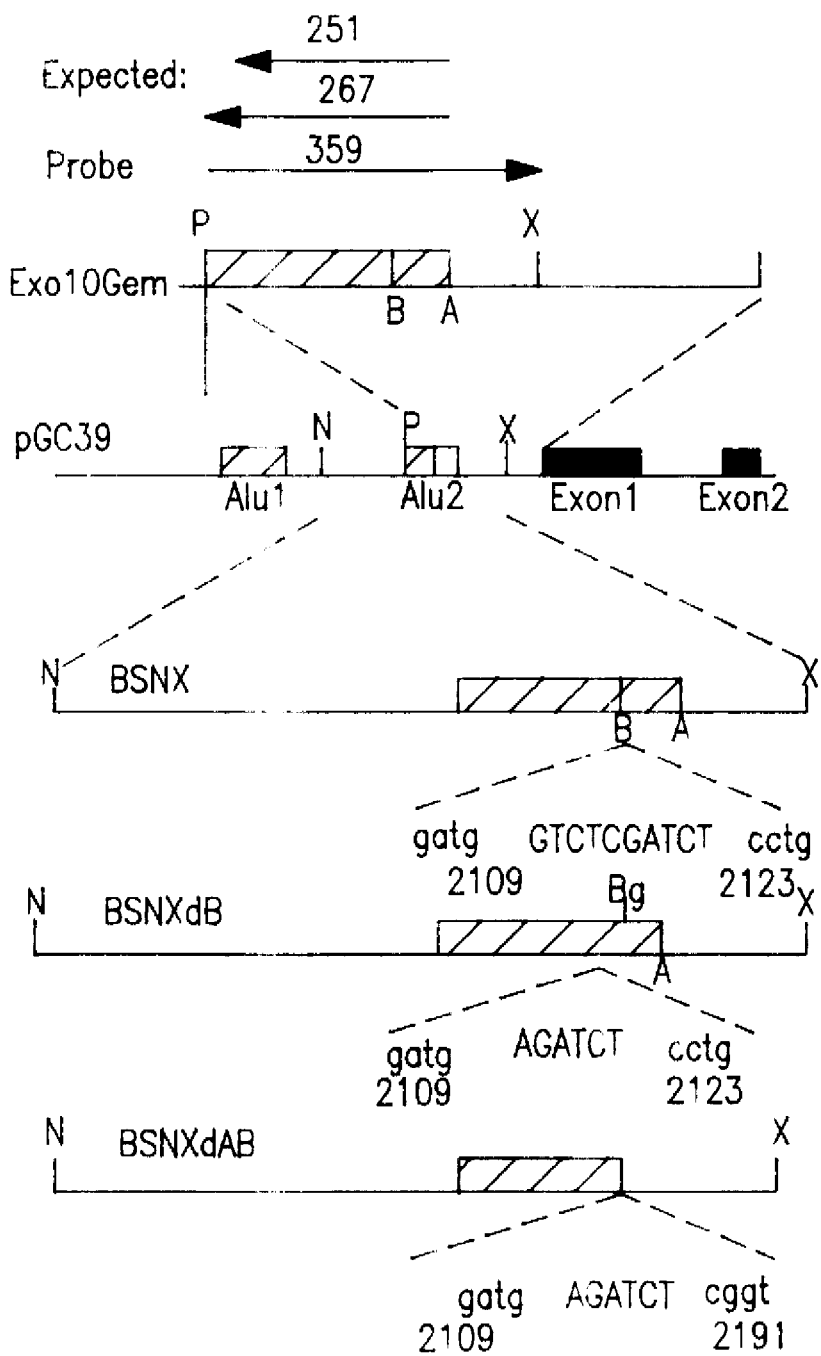
FIG. 5A shows a schematic representation of the inserts introduced into the pGC39 plasmid.

In addition, a regulatory region controlling copy number-dependent expression has also been identified within the 825 bp fragment. This regulatory region is found within an Alu type repetitive sequence, at the B box site of the Alu RNA polymerase III (pol3) promoter. To identify the role of the Alu RNA polymerase III promoter within 825 bp Alu repetitive sequence, two mutations were constructed, as shown in FIG. 5A. In the dB construction, the B Box element of the polymerase III promoter was inactivated by substitution with a BglII site as described below. In the second construction, both the A and B box elements and the region between the two elements were deleted. These constructions were transcribed in vitro, and it was determined that mutations in the B box or deletion of both the A box and the B box abolished RNA polymerase III transcription of the Alu element.

When various constructions containing the A and B box mutations were used to generate transgenic mice, it was determined that the B box mutation of the K18 Alu polymerase III promoter abolished copy number-dependent expression but did not destroy integration site-independent expression. However, the 3' flanking fragment must be absent to see this effect. This is indicated in the expression of the K18-NBX fragment shown in FIG. 8. The experiments described in Example IID below established that integration site-independent expression requires the 825 bp fragment including the Alu sequence proximal to the start site but does not require the active transcription of the repeated sequence by RNA polymerase III. These experiments further suggest that transcription of the Alu sequence by RNA polymerase III is required to achieve full transcriptional insulation of K18 or another transgene co-integrated with these fragments.

Figure 11:
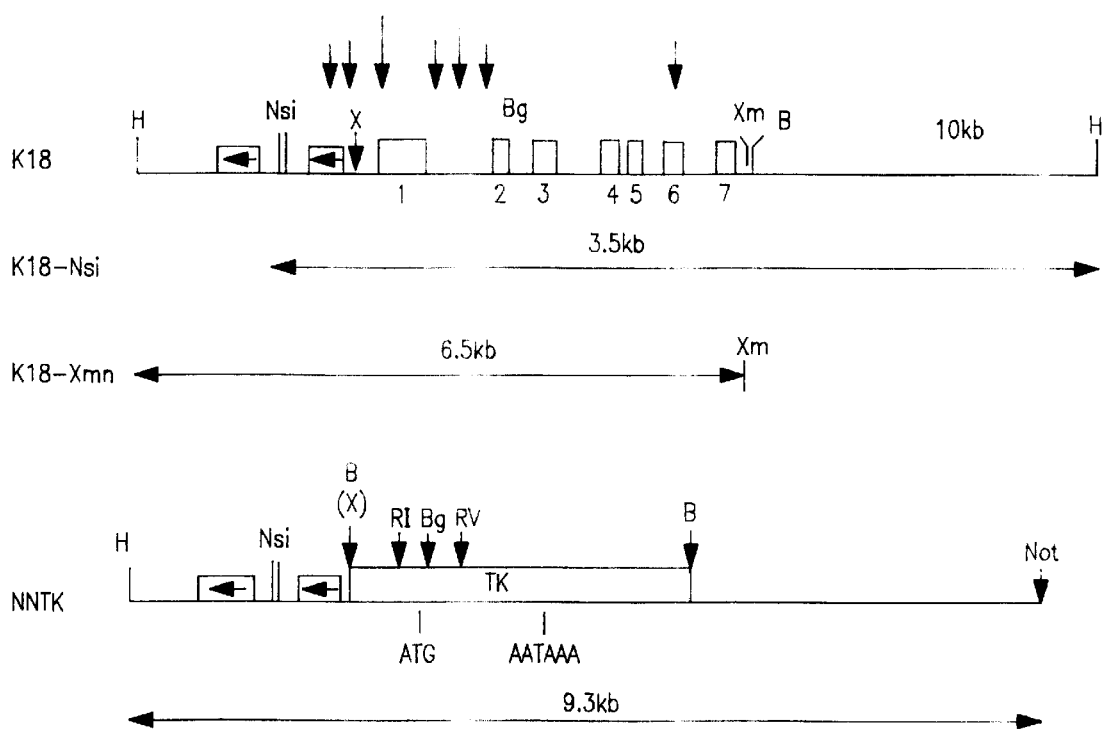
FIG. 11 shows a schematic representation of the NNTK vectors which includes the HSV TK gene flanked by the 5' and 3' regulatory regions of the K18 gene.

It has also been established that the K18 flanking regions confers site-independent and copy number dependent expression when co-integrated into an animal with transgenes other than the K18. This is demonstrated in Example IV below. In one embodiment, herpes simplex virus thymidine kinase gene (HSV TK) was inserted between the distal flanking sequences of the K18 gene as shown in FIG. 11. The HSV TK gene was inserted between the K18 5' region upstream of the XhoI site (X) at nucleotide position 2284 and the K18 3' region downstream of the BamHI (B) site at nucleotide position 6524. The 5' region includes the 825 bp fragment. The 3' region contains all of the 3.5 kb fragment responsible for transcriptional control of a transgene. HSV TK was expressed in transgenic mice in a copy number-dependent and site integration-independent manner, as described in Example IV below.

Figure 10:
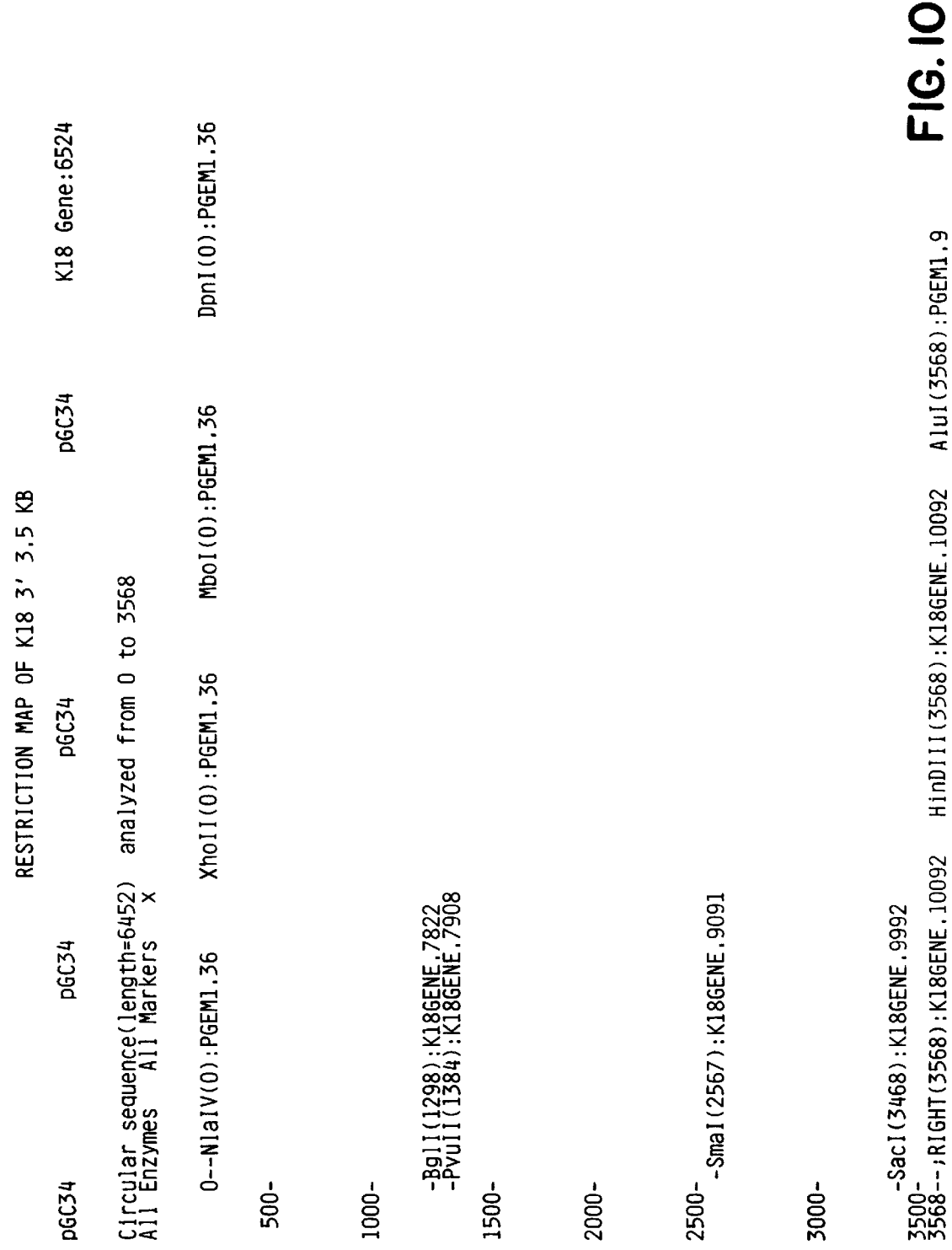
FIG. 10 shows a restriction site map for the unsequenced portion of the 3.5 kb K18 3' flanking fragment, which is located immediately 3' of the coding portion of the K18 gene.

Therefore, the 825 bp fragment and 3.5 kb fragment derived from the K18 flanking regions together confer both integration site-independent and copy number-dependent expression on a transgene when co-integrated in a 5' and 3' flanking position with the transgene. The sequence of the 825 bp fragment (Sequence I.D. No. 1) between nucleotide 1460 inclusive and nucleotide 2283 inclusive is shown in FIG. 9. A restriction map of the unsequenced portion of the 3' flanking sequence between the BamHI site, nucleotide 6524, and the HindIII site 3' end of the 10 kb K18 gene, nucleotide 10092, is shown in FIG. 10. The portion of the 3' flanking region between the XmnI site and the BamHI site has previously been sequenced and is not included in the restriction map (see Kulesh et al. (1989), supra).

The present invention also provides vectors containing the K18 derived DNA fragments. Transgenes of interest are fused to the 825 base pair fragment or 3.5 kb fragment or inserted between the 825 base pair fragment and the 3.5 kb 3' flanking sequence. The resulting DNA constructions can be injected directly into fertilized eggs to produce transgenic animals or can be introduced into cells by transfection methods such as electroporation to produce cultured cells containing the constructions. This is accomplished according to methods known in the art, such as those described in detail in the Examples below. The presence of the 5' and 3' flanking fragments adjacent to a transgene will confer integration site-independent and copy number-dependent expression on that transgene, as shown for the HSV TK gene in Example IV below. The gene to be expressed includes its coding sequence and its promoter region, as described for the HSV TK gene, or alternatively can include a promoter region from another gene.

Very few genes are presently known to be expressed independently of the sites of integration in transgenic mice. Therefore the K18 derived flanking sequences will allow for expression of a much larger number of transgenes in animals.

The vectors of the present invention also include plasmids which can be transfected into cell lines according to methods known in the art, such as is described in Example I below. Cells containing the vectors of the present invention can be used to replicate the plasmids, or as a convenient test system to verify transcription of the gene.

The vectors of the present invention also includes vectors appropriate for gene therapy using the gene to be expressed flanked by one or both of the regulatory fragments. The inclusion of these fragments in the vector used for gene therapy is useful for enhancing the expression of the gene in the subject. Therefore, DNA constructions containing any one of a number of promoters and coding genes can be placed between or adjacent to one or both K18 flanking sequences to increase regulated expression in animals.

The present invention also provides transgenic animals generated from the vectors described above. These animals contain transgenes flanked either by the 5' or the 3' fragments or both. Such animals include, for example, the transgenic mouse strains described below containing the vectors shown in FIG. 1 and 11. These animals are generated according to methods known in the art such as those described in Example I below.

The present invention also provides a method of conferring integration site-independent expression or copy. umber-dependent expression on a transgene by flanking the transgene with one or both of the fragments described above. Preferably both the 825 bp fragment and the 3.5 kb fragment are provided at the 5' and 3' flanking positions of a transgene and this construction used to generate transgenic animals.

The invention will now be described in greater detail by reference to the following non-limiting examples. These examples are intended to illustrate but not limit the invention.

EXAMPLE I

Methods and Materials

A. Construction of K18 Vectors

Human DNA fragments from cultured HeLa cells of approximately 10 kb size were generated by digestion with HindIII restriction enzyme and cloned into the Charon 30 lambda phage according to Kulesh et al., *Mol. Cell. Biol.* 8:1540–1550 (1988), which is herein incorporated by reference. After isolation of the phage DNA containing the K18 gene, the genomic fragment was excised and subcloned into the pGEM1 plasmid vector (Promega Corp., Madison, Wis.) to generate the pGC1853 plasmid (ATCC accession no. 97981). The genomic fragment containing the K18 gene was then excised from this pGC1853 plasmid (ATCC accession no. 97981), as described in Kulesh et al., *Genomics* 4:339–347 (1989), which is herein incorporated by reference, and Kulesh et al., *Mol. Cell. Biol* 8:1540–1550 (1988). The RNA polymerase III (pol3) promoter of the Alu sequence proximal to the K18 promoter was mutated by deleting the B-box (K18-Db), or both the A and B-boxes (K18-DAB) elements of the split intragenic promoter, according to the procedure described in Perez-Stable et al., *Mol Cell Biol* 6:2041–20052 (1986), which is herein incorporated by reference. The deletions were constructed by PCR synthesis of two fragments, extending from the margins of the target sequence upstream beyond the restriction site for NsiI (nt 1456) or downstream beyond the unique XhoI site (nt 2281). With K18 sequences indicated in upper case, the primer pairs used were: GGT GTG CAG AAG TCA GG (Sequence I.D. No. 2) at nt 1440 and ggc aga tct-CAT CCT AGC CAA CAT GG (Sequence I.D. No. 3) at nt 2096, ggc aga tct-CTG ACC TCG TGA TACC GC (Sequence I.D.

No. 4) at nt 2124 and ATG GAC ACG GAC AGC AG (Sequence I.D.

No. 5) at nt 2300 for the B box mutation; ggc aga tct-CGG TCA AGA CTC CCA AA (Sequence I.D. No. 6) at nt 2191 and ATG GAC ACG GAC AGC AG (Sequence I.D. No. 7) at nt 2300 for the A and B box deletion. The primers flanking the deletion site created an additional BglII site. The PCR fragments were digested with BglII, ligated together, cut with XhoI and NsiI, gel purified and cloned into the K18 gene between the XhoI and NsiI sites. The fragments constructed are shown in FIG. 1.

B. Preparation of Transgenic Mice

Transgenic mice were prepared by standard procedures as previously described Abe et al., *J. Cell Biol.* 111:1197–1206 (1990), which is herein incorporated by reference, by the Transgenic Mouse Facility at the La Jolla Cancer Research Foundation, La Jolla, Calif. Strain FVB/N mouse eggs were injected the various constructs shown in FIG. 1, and transferred to CD-1 foster mothers. Founder animals identified by dot blot hybridization of tail DNAs were sacrificed without further breeding. Mosaic animals identified by immunofluorescent staining of intestine and liver sections with a K18-specific monoclonal antibody, were excluded from further analysis. All K18-XX, K18-NX and K18-NBX mice were analyzed as described below for to determine gene copy number and orientation.

C. Transfection of Cell Lines and RNA Analysis

HR9 parietal endodermal cells were transfected by the calcium phosphate precipitate method, as described in Sambrook et al., *Molecular Cloning: A Laboratory Manual,* Cold Spring Harbor Laboratory Press, Cold Spring Harbor, N.Y. (1989), which is herein incorporated by reference with 20 μg of DNA per 9 cm dish of cells. All plasmids were co-transfected with 2 μg of the PMC1NEOPA plasmid (Stratagene, La Jolla, Calif.) as described in Thomas et al., *Cell* 51:503–512 (1987), which is herein incorporated by reference, to normalize for the transfection efficiency. RNA was purified by acidic phenol extraction of cells lysed in 0.5% SDS, 20 Mm EDTA according to Sambrook et al., supra. Total RNA was treated with RNase-free DNaseI at 37° C. for 60 minutes in the presence of RNase BLOCK™ RNase inhibitor (Stratagene, La Jolla, Calif.). K18 and neo$^R$ RNAs were quantitated by RNase protection analysis using $^{32}$P-UTP labeled probes. The RNA probe for K18 RNA was a T7 RNA polymerase transcript of a 431 bp fragment of the K18 gene (XhoI at nt 2284 to XhoII at nt 2715) overlapping the RNA start site constructed according to Kulesh et al., *Genomics* 4:339–347 (1989), which is herein incorporated by reference. For the neo$^R$ probe, a 245 bp EcoRI to NarI fragment of PMC1NEOPA was subcloned first into Bluescript KS and then into the pGEM-1 vectors via a fragment generated by EcoRI and XhoI, resulting in the NeoSP6rp plasmid. For detection of the neo$^R$ RNA, the NeoSP6rp plasmid was digested with EcoRI and transcribed with SP6 RNA polymerase. Both probes together were added to RNA from transfected cells for hybridization at 43° C. Protected probe was revealed by digestion with RNases A and T1, followed by acrylamide gel electrophoresis in 8M urea nd autoradiography.

D. Nucleic Acid Analysis of Transgenic Mice Transgene copy number was determined by dot blot hybridization of 2 μg tail DNA with the K18 CDNA according to Oshima et al., *Differentiation* 33:61–68 (1986), which is herein incorporated by reference, followed by quantitation in an Ambis radioactivity image analyzer using K18 transgenic animals with known copy numbers and multiple concentrations of plasmid DNA as standards. DNA concentrations were determined fluorometrically according to Labarca et al., *Anal. Biochem.* 102:344–352 (1980), which is herein incorporated by reference. The DNA load of each dot was normalized by rehybridizing the stripped filter with a random primed total mouse DNA probe. The average signal of all dots was considered to be 2 μg of DNA. Southern blots were performed with 5 μg tail DNA from each mouse to determine the arrangement of the integrated transgenes and to confirm the dot blot quantitation. In all cases reported, the predominant integrated organization was a head to tail tandem array of duplicated unit length gene fragments.

RNA was purified from mouse organs with the use of guanidine isothiocyanate and ultracentrifugation in $CsCl_2$ according to the procedures described in Chirgwin et al., *Biochem.* 18:5294–5299 (1979), and Turpen et al., *Biotechniques* 4:11–15 (1986), both of which are herein incorporated by reference. K18 RNA was quantitated by Northern blot analysis, including K18 synthetic mRNA standards and samples from organs of K18TG mice as controls. Northern blot filters were analyzed by hybridization with the random primed K18 cDNA probe under conditions sufficiently stringent to exclude cross-hybridization with the mouse homolog, mK18 (final washes in 0.1×SSPE, 0.1% SDS at 65° C.). After appropriate exposures, the filters were stripped of probe by boiling and rehybridized with a probe for the L32 ribosomal protein RNA according to the procedures described in Celada et al., *Eur. J. Immunol.* 19:205–208, and Dudov et al, *Cell* 37:457–468 (1984), both of which are herein incorporated by reference. Signals obtained by densitometer tracing of autoradiographs for K18 were normalized to those of L32. The mean L32 value of all samples of the same organ was considered 10 μg. RNA levels were determined by interpolation of the standard curve and are presented as pg K18 RNA/10 μg total RNA.

E. Construction and Analysis of K18 Flanking Fragments with the HSV TX Gene

Herpes simplex virus thymidine kinase (TK) gene was prepared from a 417 bp fragment of the HSV TK gene defined by EcoRI and EcoRV sites. This fragment was subcloned into the plasmid pGEM1 (Promega Corp., Madison, Wis.). TK RNA was measured by RNase protection as follows. An antisense RNA probe was made from SP6 polymerase (Promega Corp., Madison, Wis.) transcription of a larger fragment of the TK gene that extended to the BamHI site at the 5' end of the TK gene fragment. Standard synthetic TK RNA was made from a third TK fragment of 532 bp defined by PstI (nt 429) and SacI (nt 961) cloned into pGemI and transcribed by SP6 polymerase. TK RNA was standardized to the ribosomal protein L32 RNA as described by Celeda et al., *Eur. J. Immunol.* 19:205–208, which is herein incorporated by reference. TK enzyme activity was measured by a standard assay according to Jamieson et al., *J. Gen. Virol.* 24:481–492 (1974), which is herein incorporated by reference, modified so that 0.4 mM TTP is included to inhibit endogenous TK according to Al-Shawi et al., *Mol. Cell. Biol.* 8: 4821–4828 (1990), which is herein incorporated by reference. Tissues extracts were prepared from frozen tissues by homogenization in 500 μl of 50 mM Tris-HCl (pH 7.5)-5 mM mercaptoethanol-5 μM thymidine. Insoluble material was removed by centrifugation at 10,000×g for 45 minutes at 4° V/ Protein concentration was determined by the method of Bradford, *Anal. Biochem.* 72:248–254 (1976), which is herein incorporated by reference.

F. In vitro Transcription of Alu Promoter Mutations

Fragments of the K18 gene containing the Alu element proximal to the K18 transcriptional initiation site and either of two mutations of the Alu RNA polymerase III promoter were subcloned into BSKS plasmids. The plasmids were transcribed in vitro in the presence of $P^{32}$-UTP with the use of partially purified *Xenopus laevis* RNA polymerase III transcription factors as previously described in Reynolds et al., *Mol. Cell. Biol.* 12:946–953 (1992), which is herein incorporated by reference. Alu transcripts were detected by an RNAse protection assay by hybridization with 100 ng of a synthetic, non-radioactive RNA probe and subsequent digestion with RNAse T1 and acrylamide gel analysis, according to Neznanov et al., supra, which is herein incorporated by reference.

EXAMPLE II

Effect of 5' and 3' Deletions on K18 Expression

A. Constructions of K18 and K18 Fragments used to Generate Transgenic Mice

The deletion of 1.46 kb of 5' flanking sequences of the 10 kb K18 gene did not alter expression in liver, intestine or kidney in transgenic mice; however, the deletion of 3.5 kb of 3' flanking sequences abrogated efficient expression in liver, as described in Neznanov et al., supra.

The effects of deletions in both the 5' flanking as well as the 3' flanking regions of the K18 gene on the expression of the gene were determined by integrating each f the constructions shown in FIG. 1 into transgenic mice as described above. The transgenic mice containing the constructions are indicated by the name of the construction. The constructions are as follows.

The K18 gene is represented at the top of FIG. 1 with exons designated by black boxes and two Alu repetitive elements indicated by the hatched boxes. The arrows above the map indicate the positions of DNAse hypersensitive site. The restriction enzyme sites shown in FIG. 1 are HindIII (H), Nsi, NsiI, Xho, XhoI, Bgl (Bg), BglII, Xmn (Xm), XmnI, BamHI.

The K18-Xmn construct is a 6.5 kb fragment generated by digestion with HindIII and XmnI, lacking the 3' 3.5 kb of the K18 gene. This deletion leaves 155 nucleotides of DNA downstream of the last exon of K18 remaining in the construct.

The K18-Nsi construct is an 8.5 kb fragment defined by digestion with NsiI and HindIII, which is missing the first 1.5 kb of the 5' flanking sequences. This deletion removes one of two Alu repetitive elements and two apparently conserved distal sequence elements but retains the DNase-hypersensitive sites in the 5' end.

The K18-Xho construct is a 7.2 kb fragment with a 2.3 kb 5' deletion of the K18 gene.

The K18-XX construct is a 4.2 kb fragment of the K18 gene with a 5' 2.3 kb deletion and a 3' 3.5 kb deletion.

The K18-dAB fragment contains a deletion of the A box and B box elements of the Alu transcription unit proximal to the K18 gene. The sequence of the region is shown in the expanded portion of the fragment. K18 sequences are indicated in lower case. The BglII site is indicated in upper case. The numbers refer to K18 base pairs using the continuous numbering convention. Transcription initiates at approximately nucleotide 2533.

The K18-dB fragment contains a substitution of a BglII site for the B box element of the Alu promoter.

The K18-NX fragment is a 5.5 kb fragment with a 1.5 kb 5' flanking fragment and a 3.0 kb fragment deleted.

The K18-NBX fragment contains the same B box substitution in the smaller fragment defined by the Nsi and the Xho sites.

All of the constructions altered the sequences outside of the transcribed region of the K18 gene and thus are expected to generate the same K18 mRNA. Northern blot analysis confirmed the expected size of the K18 mRNA for all vectors and RNAse protection analysis confirmed the correct 5' start sites on RNAs of selected animals.

B. Deletions in 5' Flanking Region

All of the mice carrying the 2.3 kb 5' deletion of the transgene (FIG. 1, K18-Xho) expressed K18 RNA with the same tissue specificity as found for K18 mice. Expression was detected in liver, intestine, kidney, lung and brain but not in spleen, skeletal muscle or heart. This can be seen in Table I (A through D), and in FIG. 2.

Table I shows RNA levels measured by Northern blot analysis for all constructions in liver (A), intestine (B), kidney (C) and brain (D). RNA values are presented as picograms K18 RNA per 10 μg of total RNA. Average (Avg) values represent the mean and standard deviation of the indicated mouse lines. The average values only for the K18, K18-Nsi (Nsi) and K18-Xmn (Xmn) lines of mice are shown. Vector designations are abbreviated by deleting the K18-designation.

TABLE I-A

K18 RNA Expression LIVER

| Vector | Line | Copy No. | pg RNA | RNA/Gene | Average |
|---|---|---|---|---|---|
| K18 | | | | | 11.9 ± 4 (n = 5) |
| Nsi | | | | | 12.4 ± 2.6 (n = 6) |
| Xmn | | | | | 2.6 ± 2.0 (n = 6) |
| Xho | 29 | 1.5 | 1.5 | 1.0 | |
| Xho | 27 | 2.2 | 2.5 | 1.1 | |
| Xho | 14 | 2.7 | 2.5 | 0.9 | |
| Xho | 16 | 6.2 | 27.0 | 4.3 | |
| Xho | 25 | 6.4 | 22.0 | 3.5 | |
| | | | | | 2.2 ± 1.6 |
| XX | 4 | 1.3 | 0.0 | 0.0 | |
| XX | 6 | 5.0 | 8.0 | 1.6 | |
| XX | 1 | 8.4 | 0.0 | 0.0 | |
| XX | 11 | 26.3 | 9.0 | 0.3 | |
| | | | | | 0.5 ± 0.8 |
| dB | 28 | 1.6 | 10.0 | 6.2 | |
| dB | 54 | 3.1 | 14.5 | 4.7 | |
| dB | 33 | 4.4 | 51.0 | 11.6 | |
| dB | 37 | 6.6 | 37.5 | 5.7 | |
| | | | | | 7.0 ± 3.1 |
| dAB | 5 | 1.0 | 4.0 | 4.0 | |
| dAB | 20 | 1.0 | 5.0 | 5.0 | |
| dAB | 15 | 4.6 | 33.0 | 7.2 | |
| dAB | 14 | 7.8 | 98.0 | 12.5 | |
| | | | | | 7.2 ± 3.8 |
| NX | 7 | 3.9 | 9.4 | 2.4 | |
| NX | 4 | 7.0 | 18.4 | 2.6 | |
| NX | 5 | 8.5 | 12.8 | 1.5 | |
| NX | 13 | 17.5 | 64.3 | 3.7 | |
| NX | 6 | 24.1 | 134.8 | 5.6 | |
| | | | | | 3.2 ± 1.6 |
| NBX | 35 | 6.8 | 37.4 | 5.5 | |
| NBX | 15 | 7.6 | 23.2 | 3.1 | |
| NBX | 1 | 24.7 | 33.2 | 1.3 | |
| NBX | 13 | 94.3 | 19.2 | 0.2 | |
| | | | | | 2.5 ± 2.3 |

TABLE 1-B

K18 RNA Expression INTESTINE

| Vector | Line | Copy No. | pg RNA | RNA/Gene | Average |
|---|---|---|---|---|---|
| K18 | | | | | 8.3 ± 2.8 (n = 5) |
| Nsi | | | | | 5.8 ± 0.8 (n = 6) |
| Xmn | | | | | 4.5 ± 5.7 (n = 5) |
| Xho | 29 | 1.5 | 4.0 | 2.7 | |
| Xho | 27 | 2.2 | 26.0 | 11.8 | |
| Xho | 14 | 2.7 | 7.5 | 2.8 | |
| Xho | 16 | 6.2 | 90.0 | 1.5 | |
| Xho | 25 | 6.4 | 24.0 | 3.8 | |
| | | | | | 4.5 ± 4.2 |
| XX | 4 | 1.3 | 0.0 | 0.0 | |
| XX | 6 | 5.0 | 0.0 | 0.0 | |
| XX | 1 | 8.4 | 0.0 | 0.0 | |
| XX | 11 | 26.3 | 13.8 | 0.5 | |
| | | | | | 0.1 ± 0.2 |
| dB | 28 | 1.6 | 10.0 | 6.2 | |
| dB | 54 | 3.1 | 19.0 | 6.1 | |
| dB | 33 | 4.4 | 68.0 | 15.4 | |
| dB | 37 | 6.6 | 64.0 | 9.7 | |
| | | | | | 9.3 ± 4.4 |
| dAB | 5 | 1.0 | 4.0 | 4.0 | |
| dAB | 20 | 1.0 | 7.5 | 7.5 | |
| dAB | 15 | 4.6 | 76.0 | 16.5 | |
| dAB | 14 | 7.8 | 115.0 | 14.8 | |
| | | | | | 10.7 ± 5.9 |
| NX | 7 | 3.9 | 4.4 | 1.1 | |
| NX | 4 | 7.0 | 4.6 | 0.6 | |
| NX | 5 | 8.5 | 8.6 | 1.0 | |
| NX | 13 | 17.5 | 54.0 | 3.1 | |
| NX | 6 | 24.1 | 60.0 | 2.5 | |
| | | | | | 1.7 ± 1.1 |
| NBX | 35 | 6.8 | 10.2 | 1.5 | |
| NBX | 15 | 7.6 | 8.6 | 1.1 | |
| NBX | 1 | 24.7 | 19.6 | 0.8 | |
| NBX | 13 | 94.3 | 60.4 | 0.6 | |
| | | | | | 1.0 ± 0.4 |

TABLE 1-C

K18 RNA Expression KIDNEY

| Vector | Line | Copy No. | pg RNA | RNA/Gene | Average |
|---|---|---|---|---|---|
| K18 | | | | | 6.5 ± 2.3 (n = 4) |
| Nsi | | | | | 9.8 ± 2.1 (n = 5) |
| Xmn | | | | | 7.7 ± 4.2 (n = 5) |
| Xho | 29 | 1.5 | 4.0 | 2.7 | |
| Xho | 27 | 2.2 | 8.0 | 3.7 | |
| Xho | 14 | 2.7 | 1.0 | 0.3 | |
| Xho | 16 | 6.2 | 75.0 | 12.0 | |
| Xho | 25 | 6.4 | 43.0 | 6.7 | |
| | | | | | 5.1 ± 4.5 |
| XX | 4 | 1.3 | 4.6 | 3.5 | |
| XX | 6 | 5.0 | 0.0 | 0.0 | |
| XX | 1 | 8.4 | 6.0 | 0.7 | |
| XX | 11 | 26.3 | 6.6 | 0.2 | |
| | | | | | 1.1 ± 1.6 |
| dB | 28 | 1.6 | 35.0 | 21.5 | |
| dB | 54 | 3.1 | 41.5 | 13.4 | |
| dB | 33 | 4.4 | 108.0 | 24.5 | |
| dB | 37 | 6.6 | 62.5 | 9.4 | |
| | | | | | 17.2 ± 7 |
| dAB | 5 | 1.0 | 5.0 | 5.0 | |
| dAB | 20 | 1.0 | 14.0 | 14.0 | |
| dAB | 15 | 4.6 | 107.0 | 23.2 | |
| dAB | 14 | 7.8 | 135.0 | 17.3 | |
| | | | | | 14.8 ± 7.6 |
| NX | 7 | 3.9 | 10.8 | 2.8 | |
| NX | 4 | 7.0 | 33.2 | 4.7 | |
| NX | 5 | 8.5 | 4.2 | 0.5 | |
| NX | 13 | 17.5 | 46.0 | 2.6 | |
| NX | 6 | 24.1 | 87.8 | 3.6 | |
| | | | | | 2.9 ± 1.6 |
| NBX | 35 | 6.8 | 65.4 | 9.6 | |
| NBX | 15 | 7.6 | 57.2 | 7.5 | |
| NBX | 1 | 24.7 | 66.4 | 2.7 | |
| NBX | 13 | 94.3 | 52.2 | 0.6 | |
| | | | | | 5.0 ± 4.2 |

TABLE 1-D

K18 RNA Expression BRAIN

| Vector | Line | Copy No. | pg RNA | RNA/Gene | Average |
|---|---|---|---|---|---|
| K18 | | | | | 4.9 ± 3.9 (n = 4) |
| Nsi | | | | | 5.0 (n = 2) |
| Xmn | | | | | 3.9 ± 1.4 (n = 6) |
| Xho | 29 | 1.5 | 0.5 | 0.3 | |
| Xho | 27 | 2.2 | 1.5 | 0.7 | |
| Xho | 14 | 2.7 | 2.5 | 0.9 | |
| Xho | 16 | 6.2 | 7.5 | 1.2 | |
| Xho | 25 | 6.4 | 7.0 | 1.1 | |
| | | | | | 0.8 ± 0.4 |
| XX | 4 | 1.3 | 0.0 | 0.0 | |
| XX | 6 | 5.0 | 0.0 | 0.0 | |
| XX | 1 | 8.4 | 0.0 | 0.0 | |
| XX | 11 | 26.3 | 0.0 | 0.0 | |
| | | | | | 0 |
| dB | 28 | 1.6 | 6.0 | 3.2 | |
| dB | 54 | 3.1 | 14.5 | 4.7 | |
| dB | 33 | 4.4 | 55.0 | 12.5 | |
| dB | 37 | 6.6 | 25.5 | 3.8 | |
| | | | | | 6.1 ± 4.3 |
| dAB | 5 | 1.0 | 5.0 | 5.0 | |
| dAB | 20 | 1.0 | 9.0 | 18.0 | |
| dAB | 15 | 4.6 | 60.0 | 13.0 | |
| dAB | 14 | 7.8 | 7.0 | 0.9 | |
| | | | | | 9.2 ± 7.7 |
| NX | 7 | 3.9 | 0.0 | 0.0 | |
| NX | 4 | 7.0 | 0.0 | 0.0 | |
| NX | 5 | 8.5 | 0.0 | 0.0 | |
| NX | 13 | 17.5 | 0.0 | 0.0 | |
| NX | 6 | 24.1 | 0.0 | 0.0 | |
| | | | | | 0 |
| NBX | 35 | 6.8 | <2.0 | 0.0 | |
| NBX | 15 | 7.6 | 0.0 | 0.0 | |
| NBX | 1 | 24.7 | <2.0 | 0.0 | |
| NBX | 13 | 94.3 | 0.0 | 0.0 | |
| | | | | | 0 |

Figures 2A, 2B:
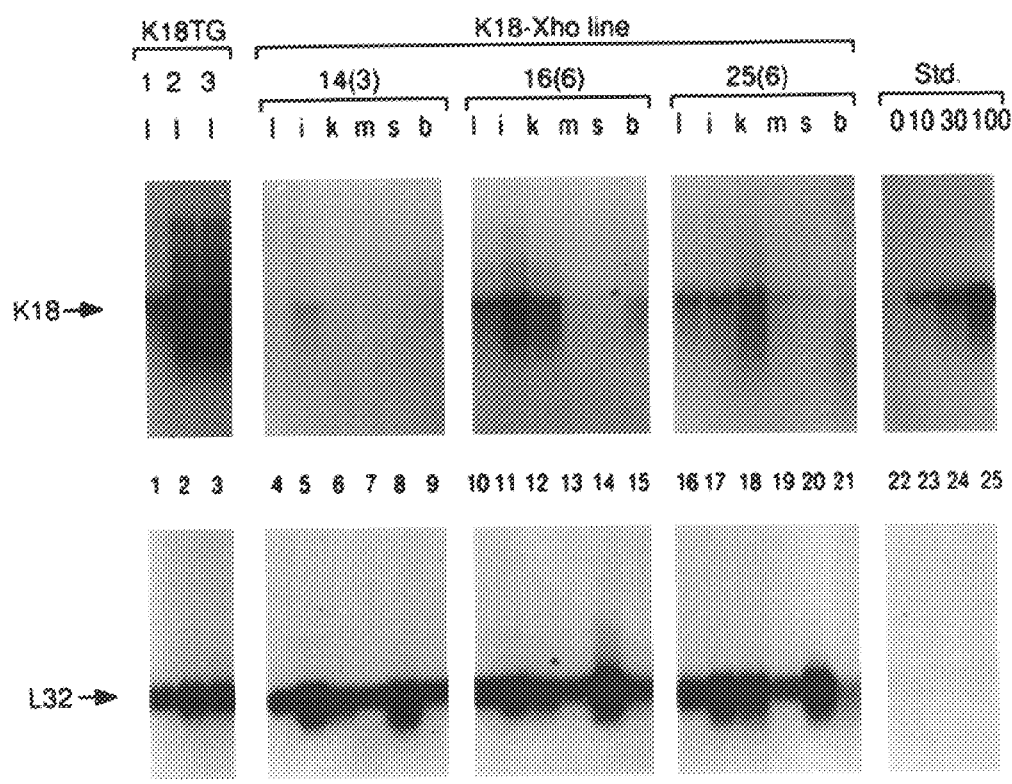
FIGS. 2A–2B show a Northern blot analysis of RNAs from K18-Xho mice obtained with K18 radioactive gene probe (FIG. 2A), and L32 ribosomal protein radioactive gene probe (FIG. 2B), in the various organs liver (l), intestine (i), kidney (k), muscle (m), spleen (s), brain (b).

FIG. 2 shows a northern blot analysis of RNAs from K18-Xho mice. Panels A and B represent the intensifier screen enhanced autoradiographic signal obtained after sequential analysis of a single filter with the K18 (panel A), and L32 ribosomal protein (panel B) radioactive gene probes. The positions of the expected signals are indicated at the left. The transgenic lines are indicated at the top. K18TG represents the K18 transgenic mice. The specific line designation with the integral copy number of the K18-Xho lines in brackets are indicated above the organ designations. The standard (std) is standard synthetic K18 mRNAs. The number indicate picograms of RNA loaded in 5 μg of carrier tRNA. Organ designations are l, liver, i, intestine, k, kidney, m, muscle, s, spleen, b,brain. 5 μg of total RNA was loaded in each lane.

Figure 3A:
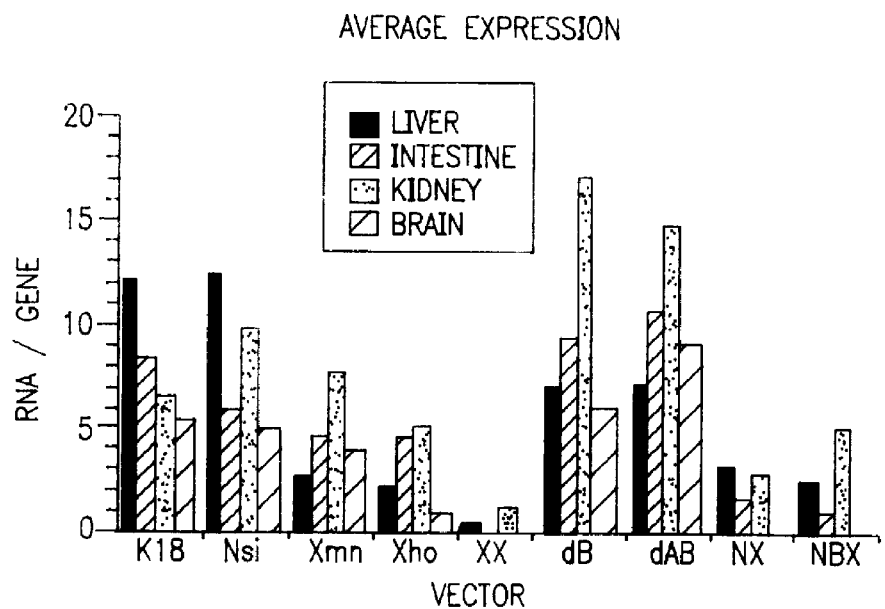
FIG. 3A shows the average expression per transgene copy in units of picograms K18 RNA/10 mg total RNA/gene in liver (l), intestine (i), kidney (k), and brain (b) for each vector shown along the y axis.
Figure 3B:
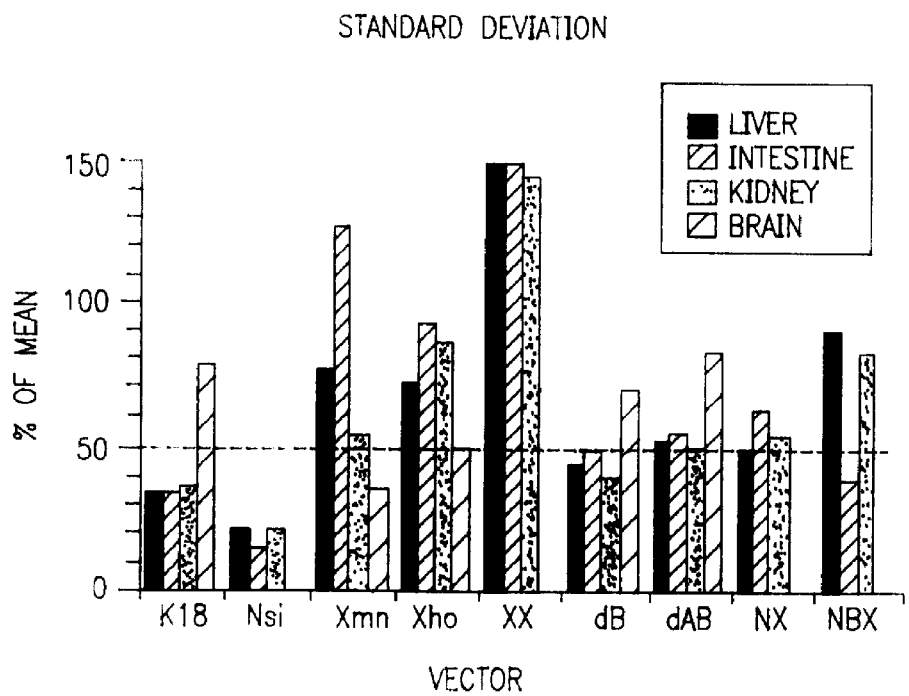
FIG. 3B shows standard deviation of the means shown in 3A.

In comparison with mice carrying either the whole gene (K18) or a smaller 1.46 kb deletion of the 5' end (K18-Nsi), the K18-Xho mice contained near normal levels in intestine and kidney, but greatly decreased levels of K18 RNA in liver and brain, as can be seen in FIG. 3A. FIG. 3A shows the average expression per transgene copy in pg K18 RNA/10 mg total RNA/gene for each of the indicated vectors. The vectors are designated as in FIG. 1 except for the deletion of the K18 prefix. Individual datum are indicated in Table 1. FIG. 3B shows the standard deviation of the means shown in panel A. The values are represented as a percentage of the mean value. Values of XX exceed 150% (see Table I). Values of about 50% or less indicate copy number dependent expression. These results appear to indicate that regulatory signals that modulate expression in liver and brain are located between the NsiI and XhoI sites within the 5' flanking sequence of the K18 gene.

The variation in expression efficiency (RNA/gene copy) was much higher in K18-Xho transgenic mice than previously characterized K18 and K18-Nsi mice (FIG. 3B and Table I). This variation is illustrated in a comparison of the standard deviation of the average of all lines of each construct as shown in FIG. 3B. The standard deviations of the averages of all K18 and K18-Nsi transgenic mice are less than 50% of the mean. In contrast, the values for intestinal RNAs and kidney RNAs of the K18-Xho mice are much in excess of the 50% level. Individual values contributing to this variation ranged from 0.3 to 12 pg K18 RNA/gene for kidney (Table I-C). Variation in liver and brain were less but the significance of the brain values may be tempered by difficulty of accurately quantitating low levels of RNA. Thus deletion of the 5' end of the K18 gene to the XhoI site, 250 bp upstream of the start of transcription, results in decreased expression in liver and brain and increased variability of expression in kidney and intestine.

C. Deletions in both 5' and 3' Flanking Fragments

FIG. 4 shows a Northern blot analysis of selected tissue RNAs of K18-NX, K18-XX, and K18-NBX transgenic lines. RNAs from liver, intestine, and kidney are shown in panels A, B and C respectively. Panels A and B represent one filter hybridized first with K18 and second with the L32 ribosomal protein probe. Standards shown in A are also appropriate for the K18 signals shown in panel B. Panel C represents a second filter analyzed in the same manner. The transgenic lines analyzed are indicated at the top of the panel, where N represents normal non-transgenic control mice, T represents K18G1, NX represents K18-NX, XX represents K18-XX, NBX represents K18-NBX, STDS represents synthetic K18 mRNA standards. K18 genes represents the nearest integral copy numbers shown in Table I.

Transgenic mice containing deletions of both the 5' and 3' ends of the K18 flanking sequences (K18-XX), expressed little or no K18 RNA in any tissue, as shown in FIG. 4. Low levels of RNA were detected in the livers of only two of the four transgenic lines, as can be seen in Table I-A. RNA was detectable in the intestine of only one of the lines, as can be seen in Table I-B. These results are in contrast with all other K18 transgenic constructions which resulted in K18 RNA in the livers, intestines and kidneys of every transgenic animal. For example, deletion of the 2.3 kb 5' flanking sequences to the XhoI site results in loss of copy number-dependent expression but every transgenic mouse line still expressed the transgenes (Table I). Similarly, all transgenic animals carrying the 3' deletions (K18-Xmn) expressed detectable levels of RNA in permissive tissues, although at low levels in the livers. These results indicate that expression is dependent upon inclusion of either the 5' or 3' flanking fragments.

The lack of expression of the K18-XX transgenes is thought to be due to position effects of the sites of integration. Because transgenes are normally found as tandemly duplicated, head to tail arrays of the injected fragments, the inclusion of either flanking element would result in the placement of the element both upstream and downstream of most gene copies in the array. Inclusion of either the 5' or 3' flanking fragments is apparently sufficient to ensure expression. However, the loss of the linear dependence of RNA expression on gene copy number suggests additional, tissue dependent regulatory elements present in both flanking elements.

D. Mutations within the 5' Flanking Fragment

1. In vitro expression

The most prominent sequence element located between the NsiI and XhoI sites at the 5' end of the K18 gene is an Alu type repetitive sequence. Two DNase hypersensitive sites in K18 transgenic liver nuclei have been mapped to this region. Two mutations within the Alu sequence were constructed, as shown in FIG. 5A.

FIG. 5A shows schematic representations of inserts of the plasmids indicated. The pGC39 plasmid insert represents the 5' 3.9 kb of the K18 gene. The two Alu sequences are indicated by the hatched boxes. K18 exons are indicated by the solid boxes. Restriction enzyme sites of NsiI (N), PstI (P), and XhoI (X) are shown. The BSNX series of plasmids represent the NsiI to XhoI fragment of the K18 gene. The positions of the A box (A) and B box (B) elements of the Alu RNA polymerase III promoter are indicated in the BSNX map. Alteration of the B box to a BglII site is indicated in the sequence below the map for BSNXdB and the deletion of the region from the beginning of the B box to the end of the A box is indicated in the sequence below the BSNXdAB plasmid. At the top of the figure the non-radioactive probe (probe) is indicated. This probe is derived from the transcription of the XhoI cut Exo10 Gem plasmid. The radioactive fragments derived the RNA polymerase III transcription of the Alu sequence after hybridization with the probe and digestion with RNAse T1 are indicated by the top two arrows, along with their expected size in nucleotides. The protected fragment from the RNA polymerase III transcription of the Exo10Gem are expected to be 16 nucleotides longer than those from the other plasmids because of additional polylinker sequences included in the probe.

FIG. 5B shows an RNAse protection analysis of Alu transcription in vitro, performed according to the method described above. RNA derived from the in vitro transcription of the plasmids indicated at the top of FIG. 5B were hybridized to non-radioactive Alu probe, digested with RNAase T1, resolved by electrophoresis in an acrylamide gel containing 8M urea, and detected by intensifier screen enhanced autoradiography. The size markers are indicated as M at right in nucleotides. A synthetic radioactive transcript P is the same size as the non-radioactive probe. Exposure times for lanes 1 to 3 and lanes 4 to 9 were one hour and 18 hours respectively. The numbers on the left edge indicated the estimated size of the protected fragments which are in good correspondence to the sizes expected. Note that no detectable transcripts were generated from the BSNXdB and BSNXDAB plasmids or from control pGEM1 or BSLSM13+ plasmids.

FIG. 5C shows an RNAse protection analysis of RNA produced when HR9 cells were transfected using the standard calcium phosphate precipitate method with the mixture of K18 constructions shown in FIG. 1, as well as the pMClneopA standard plasmid. 10 µg of RNA isolated from the cells after transfection with the K18 (lanes 1 to 3), K18-dB (B, lane 4), and K18-dAB(AB, lane 5) plasmids was analyzed using RNAse protection analysis using simultaneous hybridization with probes for the neo gene and the K18 first exon. After electrophoresis under denaturing conditions, the protected fragments were detected by intensifier screen enhanced autoradiographic exposures to X-ray films. Addition of K18 probe, neo probe, or both to the RNA is indicated in the Figure. The positions of the K18 and neo protected fragments are indicated at the left. C indicates a control of 10 µg of tRNA. 10 pg of synthetic K18 mRNA standard is Std. The K18 synthetic standard is slightly shorter than the authentic K18 mRNA. The relative activity of the different constructs is judged by the intensity of the K18 signal relative to the neo signal.

In the dB mutation the B box element of the RNA polymerase III promoter (as defined by Perez-Stable et al., *Mol. Cell. Biol.* 6:2041–2052 (1986), which is herein incorporated by reference), was inactivated by substitution with a BglII site and the deletion of two nucleotides, as is shown in FIG. 1 and FIG. 5A. In the second construction, both the A and B box elements and the region between the two elements was deleted, as is shown in FIG. 1 and FIG. 5A. To confirm the effectiveness of these mutations, both constructions were tested by in vitro transcription in a RNA polymerase III system according to Reynolds et al., *Mol. Cell. Biol.* 9:355–364 (1992). In vitro transcription of all plasmids that contained the Alu element located proximal to the K18 transcription start site resulted in RNAs with 5' ends corresponding to those expected for the RNA polymerase III promoter as seen in FIG. 5B, lanes 1 to 3. Mutation of either the B box or deletion of both the A and B boxes completely abolished RNA polymerase III transcription of the Alu element as shown in FIG. 5B, lanes 4 and 5. When replaced within the context of the whole K18 gene, these mutations did not effect expression of the K18 gene in transient transfection of L cells, as shown in FIG. 5C.

2. Expression in Transgenic Mice

To test the effect of the mutations constructed as described above on integrated forms of the genes, transgenic mice were generated from two fragments of the K18 gene containing the mutations. The K18-dB and K18-dAB mice contained the B box mutation (dB) and the A and B box deletion (dAB) respectively within the context of the previously tested K18-Nsi fragment (shown in FIG. 1). Use of the NsiI fragment eliminated the potential complication of a second Alu sequence located upstream of the targeted proximal Alu sequence.

Figure 6A:
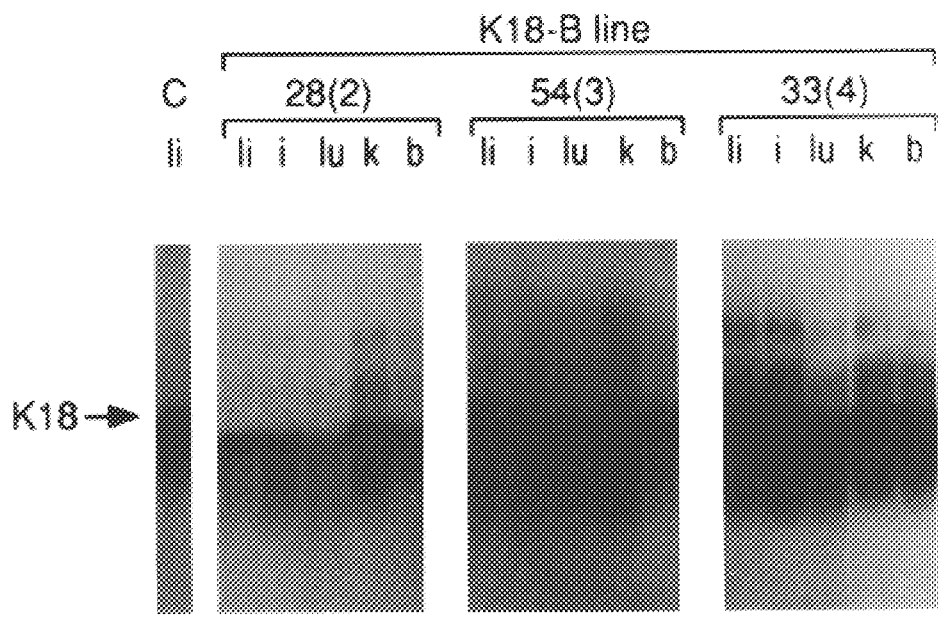
FIGS. 6A–6B show a Northern blot of RNAs from the liver, intestine, lung, kidney and brain of K18-Db transgenic mice, where
Figure 6B:
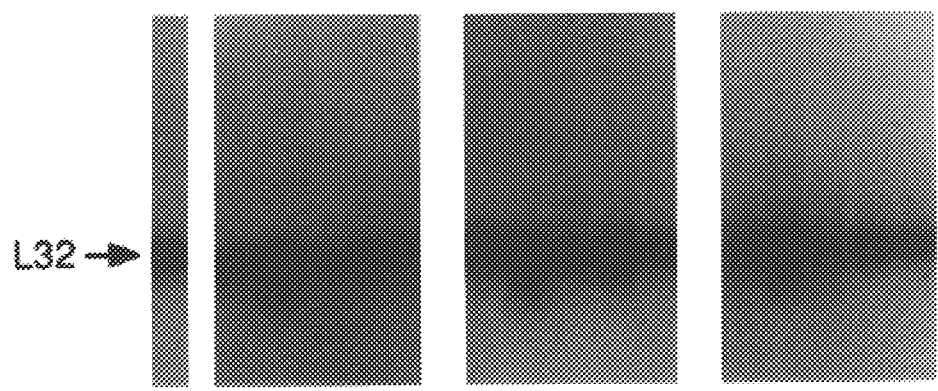
Figure 7A:
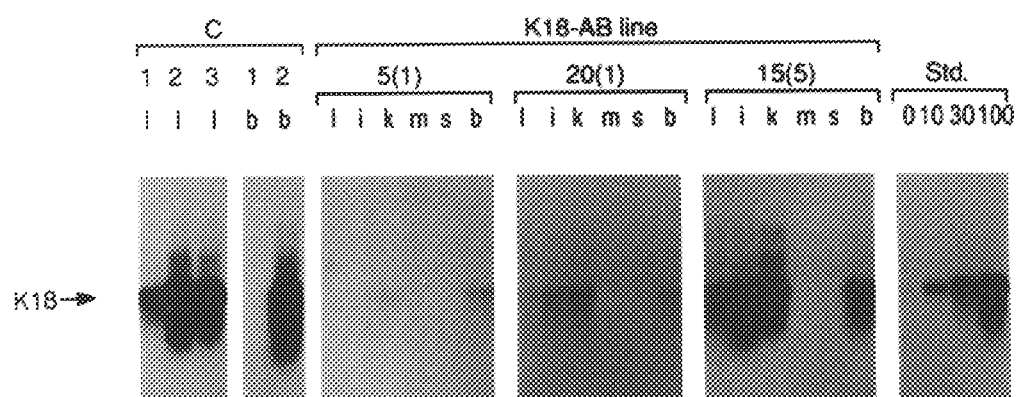
FIGS. 7A–7B show a Northern blot analysis of RNAs from the liver, intestine, lung, kidney and brain of K18-DAB transgenic mice, where
Figure 7B:
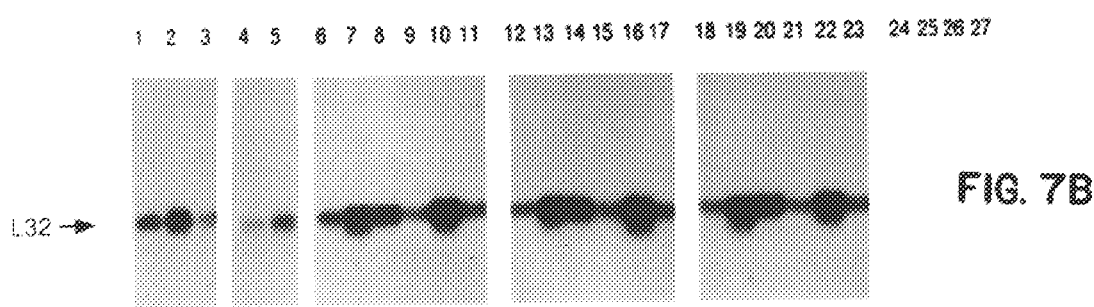

Northern blot analysis of the RNAs from three K18-dB and four K18-dAB transgenic mice are shown in FIGS. 6 and 7. FIG. 6 shows a Northern blot analysis of the RNAs from various organs of K18-dB transgenic mice. FIG. 6A represents the enhanced autoradiographic signal obtained after the sequential hybridization of a single filter with the K18 gene probe and FIG. 6B represents the signal after hybridization with L32 ribosomal protein gene probe. The position of the expected hybridization signal is indicated at left. 5 µg of RNA from the indicated organs was loaded in each line. K18-dB transgenic lines are indicated by the numbers above each set of lanes with the integral copy number indicated in brackets. Also analyzed was a K18 transgenic RNA control (C) from a K18TG1 animal, constructed according to Abe et al., *J. Cell Biol.* 111:1197–1206 (1990), which is herein incorporated by reference.

FIG. 7 is a Northern blot analysis of the RNAs from various organs of K18-dAB transgenic mice. 7A is the enhanced autoradiographic signal obtained after the sequential hybridization of a single filter with the K18 gene probe and 7B is the signal obtained with the L32 ribosomal protein gene probe. The position of the expected hybridization signal is indicated at the left. 5 µg of RNA from the organs indicated in each lane was loaded. K18-dAB transgenic lines are indicated by the numbers above each set of lanes with the integral copy number indicated in brackets. Also analyzed were K18 transgenic RNA controls (C) from K18TG1 (1), K18TG1(2) and K18TG3 (3) animals, three independent lines of K18 transgenic mice constructed according to Abe et al.(1990) supra, and synthetic mRNA standards (Std) at 0 to 100 pg.

Values for all individual mice are listed in Table I. In most respects the two mutations of the Alu RNA polymerase III promoter had little effect on K18 RNA expression. Like the wild type K18-Nsi mice, the K18-dB and K18-dAB mice expressed the K18 RNA in liver, intestine, kidney, lung and brain. Spleen, heart and skeletal muscle remained negative. However, quantitatively, both the K18-dB and K18-dAB mice expressed higher levels of RNA in kidney than the comparable K18-Nsi mice. (see FIG. 3A). Expression in liver, intestine and kidney was proportional to copy number as indicated by the variation of the expression per gene (FIG. 3B). These experiments suggest that transcriptional activity of the Alu RNA polymerase III activity is not essential for either efficient tissue specific expression or integration site-independent, copy number-dependent expression, when assayed in the presence of the 3' flanking sequences of the K18 gene. However, because the inclusion of either the 5' or 3' flanking sequences with the body of the K18 gene ensures expression in intestine and kidney (in FIG. 3A, compare K18-Xmn and K18-Xho in intestine and kidney to K18-XX), it was possible that any effect of mutation of the Alu polymerase III promoter was masked by the presence of the 3' flanking elements.

In order to evaluate the effect of the mutations in the Alu RNA polymerase III promoter in the absence of additional Alu elements in the 3' flanking sequence, additional animals were generated having the B box mutation but without the 3' flanking sequences. These are designated K18-NBX, as seen in FIG. 1. A second set of control mice, K18-NX, carried the same wild type fragment.

Representative Northern blot analysis of these animals are shown in FIG. 4. Individual animal data are presented in Table I and a summary of all animals is shown in FIG. 3. As expected, from including the 3' deletion, expression in liver was decreased in both sets of animals (FIG. 3). In addition, expression in intestine and kidney was also low and no expression was detected in the brains of transgenic mice carrying either construction. While the average level of expression of the available transgenic lines reveals no difference between the K18-NX and K18-NBX mice in liver, intestine or kidney, the copy number dependence of expression of the two sets of animals is quite different.

FIG. 4 and Table I compare the standard deviation of the RNA expression per gene copy of the K18-NX and K18-NBX mice. The efficiency of expression of the K18-NBX mice progressively decreased with increasing copy number as seen in FIG. 8.

Figure 8:
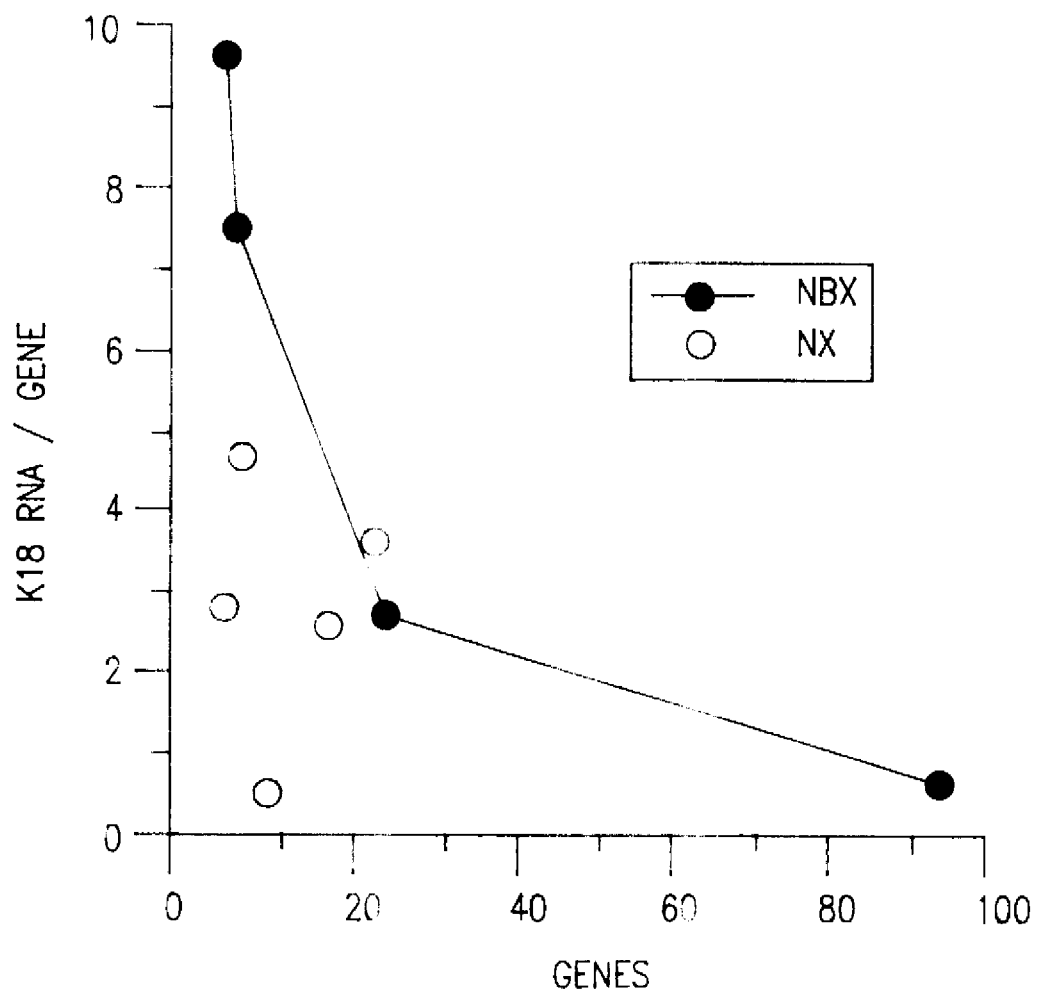
FIG. 8 shows the transcriptional efficiency in terms of pg K18 RNA per gene expressed as a function of numbers of copies of the K18 gene in mouse kidney.

FIG. 8 shows decreasing transcriptional efficiency of K18-NBX mice with increasing copy number. The efficiency of expression in kidney expressed as pg K18 RNA/gene copy is plotted as a function of the copy number. Each point represents a separate transgenic founder. The data shown in FIG. 8 suggests that the NBX fragment did not ensure that all copies of the tandem arrays of transgenes are efficiently expressed. The standard deviations of liver and kidney RNA/gene approached 100% for K18-NBX mice while those for the control K18-NX mice were similar to the 50% or less values found for the other copy number dependent fragments: K18, K18-Nsi, K18-dB and KIB-dAB. The B box mutation leads to greater variation in the efficiency of expression and a striking decrease in efficiency of expression as copy number increases (FIG. 8). However, both the K18-NX and K18-NBX transgenes are expressed in the same tissues as the control K18 transgenes.

It summary, it was found that all of the. transgenic mice tested analyzed above except for those derived from the K18-XX vectors expressed detectable levels of K18 RNA in appropriate tissues and did not show ectopic expression except possibly for expression in the brain. It can therefore be concluded that if there are regulatory elements essential for tissue specific expression of the K18 gene, they are within the 5 kb fragment bounded by the NsiI site 1075 bp upstream of the transcription start site and the XmnI site 155 bp downstream of the last exon.

EXAMPLE III

Sequences and Restriction Map of K18 Flanking Regions

The full-length human keratin K18 gene was previously isolated as described in Example I. The entire coding region of the K18 gene was then sequenced. The sequencing was performed according to Sanger et al., *Proc. Natl. Acad. Sci. USA* 74:5463–5467 (1977), as described in Kulesh et al., *Genomics* 4:339–347 (1989), both of which are herein incorporated by reference. The translation initiation codon ATG that begins the open reading frame of exon 1 for the entire K18 gene is located at approximately nucleotide 2533, using the open numbering convention.

FIG. 9 shows the sequence of the 5' 825 bp region between the proximal NsiI site, at nucleotide 1460 inclusive and the XhoI site, at nucleotide 2283 inclusive. (Sequence I.D. No. 1). The locations of the B box and A box are indicated by the underlined sequences.

FIG. 10 shows a restriction map of the unsequenced portion of the 3' flanking 3.5 kb fragment of the K18 gene. The 3' flanking region of the K18 gene from the BamHI restriction site to the HindIII restriction site (as shown in the schematic diagram of FIG. 1) was subcloned into a pGEM-1 plasmid (Promega Corp., Madison, Wis.), designated pGC34, according to Kulesh et al., (1989), supra. This fragment extends from K18 nucleotide 6524 to K18 nucleotide 10092. The restriction sites of this fragment were then identified using restriction analysis according to standard procedures, as shown in FIG. 10. The 3' flanking region between the XmnI site, nucleotide 6468, and the BamHI site, nucleotide 6524, was previously sequenced (Kulesh et al., (1989), supra) and is as follows: TTGTC TTCTTTTGGC TGTTTTCATT GTGCACAAAT GCCCTAACCC AACAGTCCCA TCCCTGATCC AGCAGAAACC ACCTCTGACC CCTGAGGTTT CATATAGATT GGGGT-GTAGA AGGAAGAGGG ATCTGTATTC TTGGAAA-CAC TTCTGAGAGA CAGAGGAGGG AGCAGTAGAT GTGATGGGTC ACAGGCTGTG GGGATCC (Seq ID No: 8). Therefore, this segment of the 3.5 kb fragment was not included in the restriction analysis. However, the entire 3' flanking 3.5 kb fragment is considered to extend from the XmnI restriction site, nucleotide 6468 to the HindIII restriction site, nucleotide 10092.

EXAMPLE IV

Use of K18 5' and 3' Flanking Regions to Express HSV TK in Ttansgenic Mice

To test whether the characteristic of position-independent, copy number-dependent expression was independent of the regulation of the K18 gene, the herpes simplex virus thymidine kinase gene (HSV TK) including promoter and coding elements was inserted between the distal flanking sequences of the K18 gene, as shown in FIG. 11. This vector lacks the proximal promoter and all internal regulatory elements of the K18 gene. This vector was constructed as described in Example I.

FIG. 11 shows the NNTK vector which includes the HSV TK gene (TK) flanked by the 5' and 3' flanking regions of the K18 gene. The TK gene is represented by the open box. Positions of the ATG translation initiation codon and the polyadenylation signal are indicated below the map. Additional restriction enzyme sites are indicated for EcoRI (RI), BamHI (B), BglII (Bg), EcoRV (RV), NotI (Not), and XhoI (X).

Figure 12:
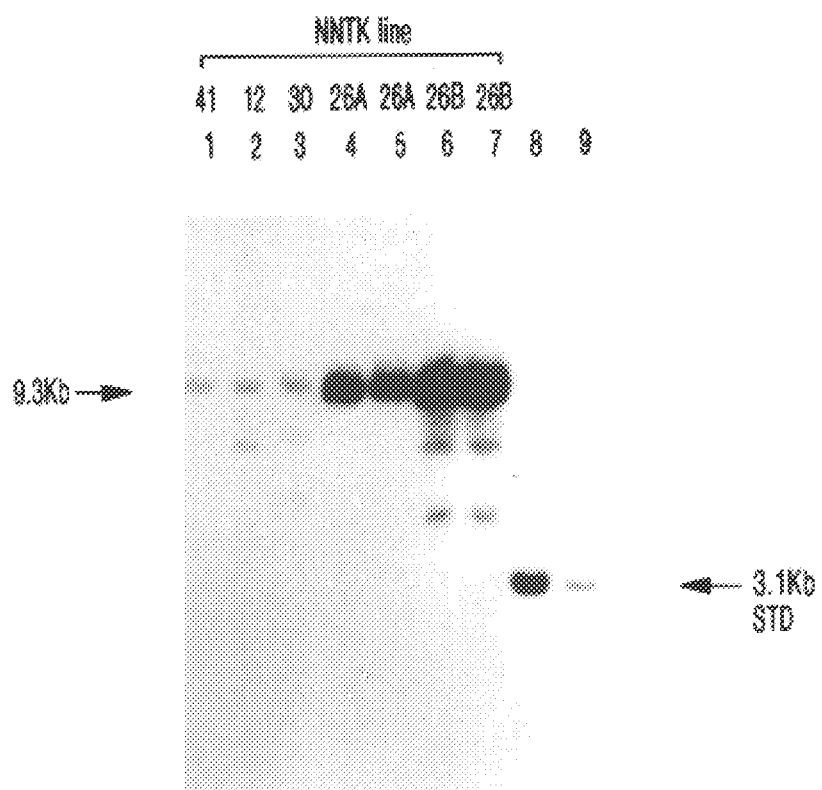
FIG. 12 shows a Southern blot of the DNAs of NNTK transgenic mice.

Two nonmosaic male and two nonmosaic transgenic female mouse founders were identified. Both males were sterile and were sacrificed for analysis. Male progeny of two female founders were analyzed. One of these strains, NNTK-26, integrated transgenes into two different places. Subsequent breeding of the founder resulted in the segregation of two different integration sites, thus generating an additional different line. Southern blot analysis of the five NNTK lines is shown in FIG. 12. In lanes 1 to 7, 10 μg of DNA from the indicated lines of mice was digested with BglII, separated by agarose gel electrophoresis, blotted to a charged nylon membrane, and hybridized with a random primed fragment of the 5' end of the HSV TK gene. Two different animals of lines NNTK-26A and NNTK-26B were included (lanes 4 and 5, and lanes 6 and 7). Lanes 8 and 9 contained the equivalent of six and two copies per cell of the NNTK fragment used for the generation of the transgenic mice mixed with 5 μg of normal mouse DNA and digested with BglII. The 9.3 kb size of the major hybridizing band is the expected size for head-to-tail duplications of the injected fragment. Both the intensities of the 9.3-kb fragments and the presence of smaller fragments found in the NNTK-26B mice confirm the different integration sites responsible for the segregation of the NNTK-26A and NNTK-26B lines of mice. The probe hybridizes to the 3.1 kb 5' portion of the nonduplicated NNTK fragment.

In a survey of different tissues, TK RNA was detected only in testes and, at a much lower level, in brain. However, like K18 and K18-Nsi transgenic mice, every NNTK transgenic mouse expressed detectable levels of transgenic RNA. Representative results of an RNase protection assay are shown in FIG. 13.

Figure 13A:
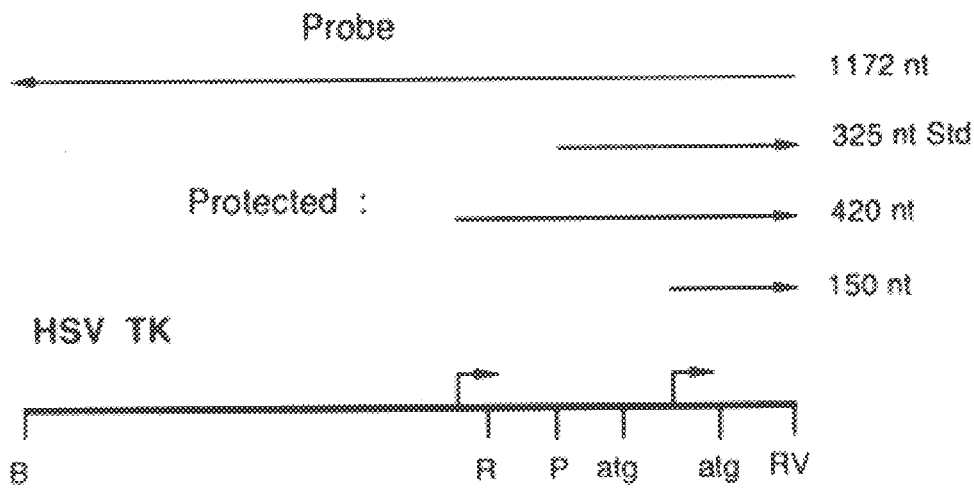
FIG. 13A shows a partial map of the 5' end of the HSV TK gene.
Figure 13B:
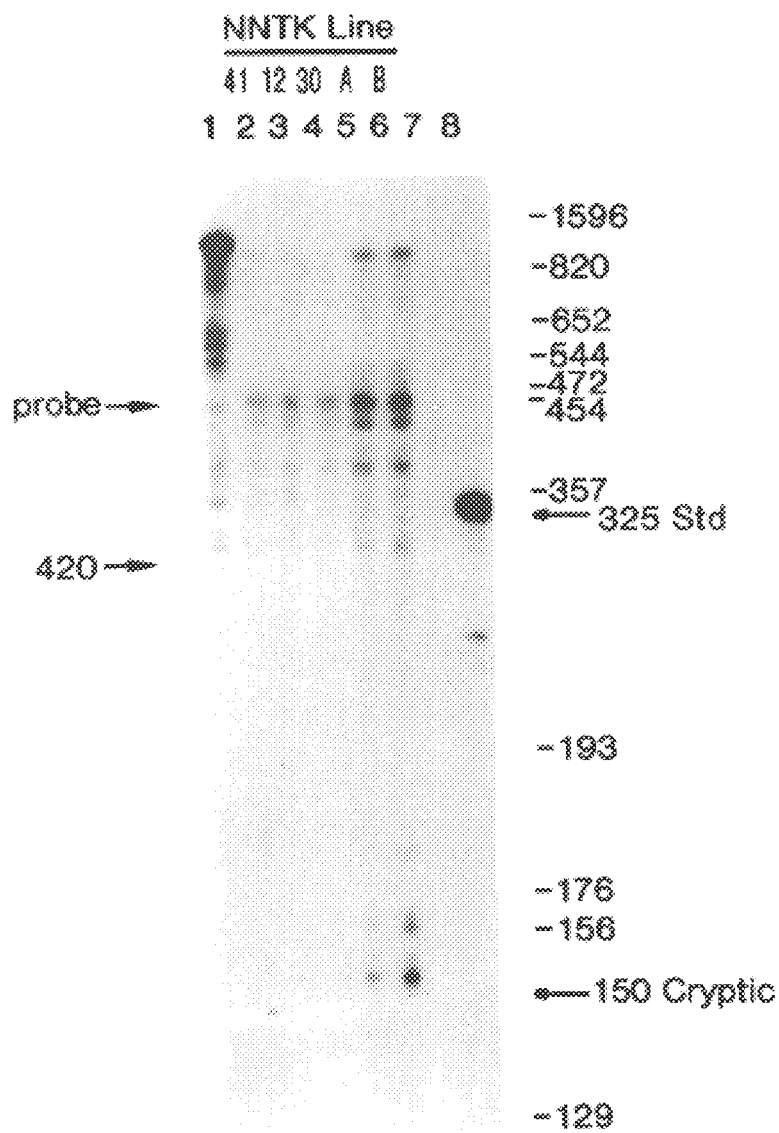
FIG. 13B shows an RNA analysis of herpes simplex virus thymidine kinase (HSV TK) from the testes of five lines of transgenic mice.

FIG. 13A shows a partial map of the 5' end of the HSV TK gene, indicated by the heavy line. Putative transcriptional initiation sites and direction are indicated by the bent arrows. The portions corresponding to the probe or the nonradioactive standard RNA and observed protected fragments are shown by the thin, horizontal arrowed lines. FIG. 13B shows an RNA protection analysis from the testes of five indicated lines of transgenic mice. Total RNA was hybridized to the TK probe, then digested with RNases A and $T_1$, and analyzed by acrlyamide gel electrophoresis in 8M urea and autoradiography. 10μg of RNAs for each line except 26B (lane 6, 6μg) was used. RNA amounts were standardized independently by hybridization with ribosomal protein L32. Lane 7 is the tRNA control, lane 8 is 4 pg of the synthetic standard TK RNA (std). The major protected fragment representing the previously reported testes-specific, internal promoter is indicated at the right (cryptic).

Figure 14A:
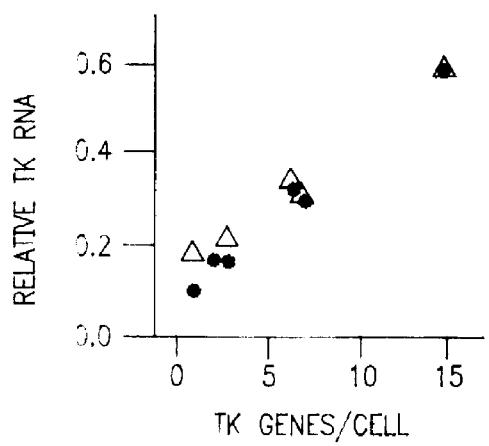
FIGS. 14A–14C show the copy number dependence of TK RNA and enzyme activity, where
Figure 14B:
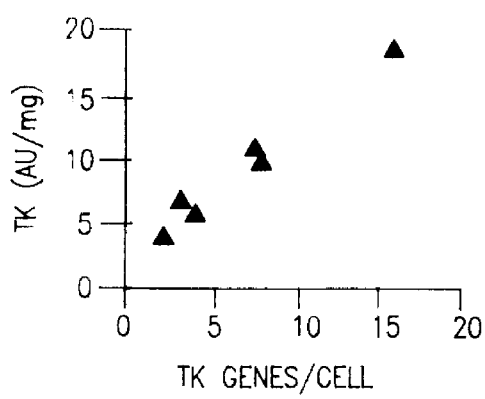
Figure 14C:
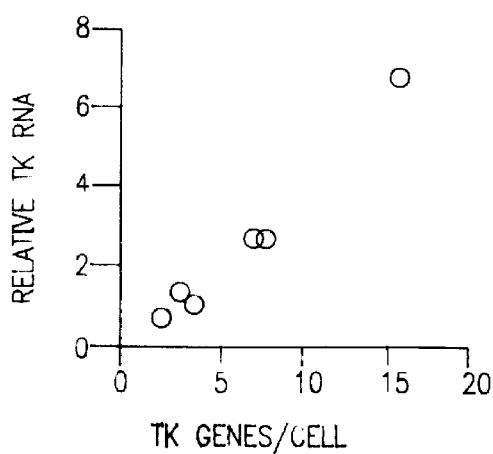

Two major sets of protected fragments were detected in the testes. The larger protected fragment of 420 nucleotides (nt) was specific for the TK RNA. The smaller fragment of about 150 nucleotides corresponds to the internal, cryptic promoter associated with the TK gene. The levels of both RNAs increased linearly with increased copy number, as shown in FIG. 14. FIG. 14 shows copy number dependence of TK RNA and enzyme activity. FIG. 14A shows relative number dependence of TK RNA per 10 μg of total RNA plotted as a function of the copy number for each transgenic line. Circles indicate the values for the 420-nt protected fragment, and triangles represent the values for the smaller 150-nt protected fragment. Values for the smaller fragment were estimated from a film exposed three times longer than that used for the longer transcript. FIG. 14B shows TK enzyme activity in arbitrary units (AU) in the testes of transgenic ales compared with the copy number of the NNTK mouse lines. FIG. 14C shows TK brain RNA estimated by RNase protection compared with the copy number of the independent lines. Values for TK RNA found in the brain was approximately 10-fold less abundant than that found in testes for any individual strain.

Therefore, it has been found on the basis of these experiments that the HSV TK gene when combined with the K18 distal flanking sequences is expressed in a copy number dependent and position independent manner, although expression is strictly restricted in tissue specificity. In addition, the NNTK vector is expressed in every transgenic mouse line. In addition, all transgenic males were sterile, as expected for elevated expression of the transgene (see Al-Shawi et al, *Mol. Cell. Biol.* 8:4821–4828 (1988), and Braun et al., *Biol. Reprod.* 43:684–693 (1990)). Therefore, it has been demonstrated that the characteristics of position-independent and copy number-dependent expression may be conferred by the distal 5' and 3' flanking sequences of the K18 gene.

While the invention has been described in detail with reference to presently preferred embodiments, it is understood that various modifications can be made without departing from the spirit of the invention. Accordingly, the invention is limited only by the following claims.

We claim:

1. An isolated 825 base pair (bp) DNA molecule derived by restriction endonuclease cleavage of plasmid pGC1853 (ATCC accession no. 97981) using NsiI and XhoI, or an equivalent DNA molecule thereof, wherein the DNA molecule confers integration site-independent and copy number-dependent expression to an operably linked transgene.

2. A DNA molecule comprising the isolated 825 base pair DNA molecule of claim 1, further comprising a transgene operably linked thereto, wherein the transgene is not the K18 gene.

3. An isolated DNA molecule comprising the nucleotide sequence set forth as SEQ ID NO: 1, provided that said isolated DNA molecule is not the K18 gene.

4. An isolated 3.5 kb DNA molecule derived by restriction endonuclease cleavage of plasmid pGC1853 (ATCC accession no. 97981) using XmnI and HindIII, or an equivalent DNA molecule thereof, wherein the DNA molecule confers integration site-independent and copy number-dependent expression to an operably linked transgene.

5. A DNA molecule comprising the isolated 3.5 kb DNA molecule of claim 4, further comprising a transgene operably linked thereto, wherein the transgene is not the K18 gene.

6. A DNA molecule comprising a transgene operably linked to a 825 bp DNA molecule and a 3.5 kb DNA molecule, said 825 bp DNA molecule derived by restriction endonuclease cleavage of plasmid pGC1853 (ATCC accession no. 97981) using NsiI and XhoI, or an equivalent DNA molecule thereof, and said 3.5 kb DNA molecule derived by restriction endonuclease cleavage of plasmid pGC1853 (ATCC accession no. 97981) using XmnI and HindIII, or an equivalent DNA molecule thereof, wherein said 825 bp and 3.5 kb DNA molecules confer both integration site-independent and copy number-dependent expression, provided that said DNA molecule is not the K18 gene.

7. A vector comprising the DNA molecule of any one of claims 1 to 6, provided that the vector does not have the construct of K18 as shown in FIG. 1.

8. A vector comprising a DNA construct selected from the group consisting of K18-Xmn, K18-Nsi, K18-Xho, K18-dAB, K18-dB, K18NX, and K18NBX, each of which is shown in FIG. 1, provided that the vector does not comprise the construct of K18 as shown in FIG. 1.

9. A vector, comprising a DNA construct NNTK as shown in FIG. 11.

10. A cell line containing the vector of claim 7.

11. A method of conferring integration site-independent expression and copy number-dependent expression on a transgene in a transgenic animal, comprising inserting the DNA molecule of any one of claims 2, 5 or 6 into the genome of said animal or an ancestor thereof at an embryonic stage of development, whereby said transgene is expressed in an integration site-independent and copy number-dependent manner.

12. A method of conferring integration site-independent expression on a transgene in a transgenic animal, comprising inserting the DNA molecule of any one of claims 2, 5 or 6 into the genome of said animal or an ancestor thereof at an embryonic stage of development, whereby said transgene is expressed in an integration site-independent manner.

* * * * *

UNITED STATES PATENT AND TRADEMARK OFFICE
CERTIFICATE OF CORRECTION

PATENT NO. : 5,840,555
DATED : November 24, 1998
INVENTOR(S) : Oshima et al.

It is certified that error appears in the above-identified patent and that said Letters Patent is hereby corrected as shown below:

Column 2,
Line 5, please delete "can 35 be" and replace with -- can be --.

Column 4,
Lines 63-64, please delete the carriage return.

Column 8,
Line 29, please delete "urea nd" and replace with -- urea and --.
Line 31, please insert carriage return after "Transgenic Mice"

Column 9,
Line 63, please delete "each f" and replace with -- each of --.

Column 15,
Line 48, please delete "BSNXDAB" and replace with -- BSNXdAB --.

Column 18,
Line 55, please delete "Ttansgenic" and replace with -- Transgenic --.

Signed and Sealed this

Twenty-sixth Day of March, 2002

Attest:

*Attesting Officer*

JAMES E. ROGAN
*Director of the United States Patent and Trademark Office*

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 825 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

| | | | | | | |
|---|---|---|---|---|---|---|
| CATTCCCTGT | CCAAATCACA | GTGTTCCACT | GAGGCAAGGC | CCTTGGGAGT | GAGGTCGGGA | 60 |
| GAGGGGAGGG | TGGTGGAGGG | GGCTCAGAGA | CTGGGTTTGT | TTTGGGGAGT | CTGCACCTAT | 120 |
| TTGCTGAGTG | AATGTATGTG | TGTGTGCATT | TGAGAGCACA | CCTCTGTATG | ATTCGGGTGT | 180 |
| GAGTGTGTGT | GAGGAAACGT | GGGCAGGCGA | GGAGTGTTTG | GGAGCCAGGT | GCAGCTGGGG | 240 |
| TGTGAGTGTG | TAAGCAAGCA | GCTATGAGGC | TGGGCATTGC | TTCTCCTCCT | CTTCTCCAGC | 300 |
| TCCCAGCCTT | TCTTCCCCGG | GACTCCTGGG | GCTCCAGGAT | GCCCCAAGA | TCCCTCCAC | 360 |
| AAGTGGATAA | TTTGGGCTGC | AGGTTAAGGA | CAGCTAGAGG | GACTCACAGG | CCATTCCACC | 420 |
| CGCACACCAC | CAGACCCCCA | AATTTCTTTT | TTCTTTTTTT | TTTGAGACAG | AGTCTCACTC | 480 |
| TGTCGCCAGG | CTGCAGTGGC | GCGATCTCGG | CTCACTGCAA | CCTCCGCCTC | CCAGGTTCAA | 540 |
| GCGATTCCCC | TTCCTCAGCC | TCCCAAGTAG | CTGAGACTAC | AGGCGTGCAC | CATCACGTCC | 600 |
| GGCTAATTTT | TTGTATTTTA | GTAGAGAGGG | GTTTCACCAT | GTTGGCTAGG | ATGGTCTCGA | 660 |
| TCTCCTGACC | TCGTGATCCG | CCCACCTAGG | CCTCCCAAAG | TGCTGAGATT | ACAGGCGTGA | 720 |
| GCCACTGCGC | CCGGTCAAGA | CTCCCAAATT | TCAAACTCGC | CAGCACCTCC | TCCACCTGGG | 780 |
| GGAGAAGAGC | ATAATAACGT | CATTTCCTGC | CCTGAAAGCA | GCCTC | | 825 |

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GGTGTGCAGA AGTCAGG                                                                                                       17

( 2 ) INFORMATION FOR SEQ ID NO:3:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

GGCAGATCTC ATCCTAGCCA ACATGG                                                                     26

( 2 ) INFORMATION FOR SEQ ID NO:4:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

GGCAGATCTC TGACCTCGTG ATACCGC                                                                  27

( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

```
ATGGACACGG ACAGCAG                                                                          17
```

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:6:

```
GGCAGATCTC GGTCAAGACT CCCAAA                                                                26
```

(2) INFORMATION FOR SEQ ID NO:7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:7:

```
ATGGACACGG ACAGCAG                                                                          17
```

(2) INFORMATION FOR SEQ ID NO:8:

(i) SEQUENCE CHARACTERISTICS:
        (A) LENGTH: 202 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:8:

```
TTGTCTTCTT TTGGCTGTTT TCATTGTGCA CAAATGCCCT AACCCAACAG TCCCATCCCT      60
GATCCAGCAG AAACCACCTC TGACCCCTGA GGTTTCATAT AGATTGGGGT GTAGAAGGAA     120
GAGGGATCTG TATTCTTGGA AACACTTCTG AGAGACAGAG GAGGGAGCAG TAGATGTGAT     180
GGGTCACAGG CTGTGGGGAT CC                                              202
```